US008313528B1

(12) United States Patent
Wensel

(10) Patent No.: US 8,313,528 B1
(45) Date of Patent: Nov. 20, 2012

(54) INTERVERTEBRAL FUSION DEVICE AND METHOD OF USE

(75) Inventor: Jeffrey Paris Wensel, Eugene, OR (US)

(73) Assignee: Spinelogik, Inc., Eugene, OR (US)

( * ) Notice: Subject to any disclaimer, the term of this patent is extended or adjusted under 35 U.S.C. 154(b) by 724 days.

(21) Appl. No.: 12/113,362

(22) Filed: May 1, 2008

Related U.S. Application Data

(60) Provisional application No. 61/040,136, filed on Mar. 27, 2008.

(51) Int. Cl.
*A61F 2/44* (2006.01)
(52) U.S. Cl. .................................................. 623/17.11
(58) Field of Classification Search ................ 623/17.11, 623/FOR. 17
See application file for complete search history.

(56) References Cited

U.S. PATENT DOCUMENTS

| | | | |
|---|---|---|---|
| 4,554,914 A | 11/1985 | Kapp et al. | |
| D312,309 S | 11/1990 | Michelson | |
| 5,015,247 A | 5/1991 | Michelson | |
| 5,484,437 A | 1/1996 | Michelson | |
| 5,505,732 A | 4/1996 | Michelson | |
| 5,522,899 A | 6/1996 | Michelson | |
| D377,095 S | 12/1996 | Michelson | |
| D377,096 S | 12/1996 | Michelson | |
| D377,527 S | 1/1997 | Michelson | |
| 5,593,409 A | 1/1997 | Michelson | |
| 5,609,635 A | 3/1997 | Michelson | |
| 5,653,761 A | 8/1997 | Pisharodi | |
| D392,387 S | 3/1998 | Michelson | |
| 5,741,253 A | 4/1998 | Michelson | |
| 5,772,661 A | 6/1998 | Michelson | |
| 5,776,199 A | 7/1998 | Michelson | |
| 5,785,710 A | 7/1998 | Michelson | |
| 5,797,909 A | 8/1998 | Michelson | |
| 5,860,973 A | 1/1999 | Michelson | |
| D425,989 S | 5/2000 | Michelson | |
| 6,080,155 A | 6/2000 | Michelson | |
| 6,096,038 A | 8/2000 | Michelson | |
| 6,120,502 A | 9/2000 | Michelson | |
| 6,120,503 A | 9/2000 | Michelson | |
| 6,123,705 A | 9/2000 | Michelson | |
| 6,136,001 A | 10/2000 | Michelson | |
| 6,139,551 A | 10/2000 | Michelson | |

(Continued)

FOREIGN PATENT DOCUMENTS

DE 199 44 681 A1 * 3/2001

(Continued)

OTHER PUBLICATIONS

U.S. Appl. No. 60/916,414, filed May 7, 2007.*

(Continued)

*Primary Examiner* — David H. Willse
(74) *Attorney, Agent, or Firm* — Adeli & Tollen, LLP

(57) ABSTRACT

Some embodiments of the invention disclose an apparatus for achieving rapid mechanical fusion between two adjacent vertebral bodies by positioning a fusion member with one or more channels between the two vertebral bodies. Once the fusion member properly positioned, one or more needles are passed through the fusion member's channels and advanced into the marrow space of the adjacent vertebral bodies. Each needle has a lumen for receiving adhesive material and supplying said material to the marrow space of the adjacent vertebral bodies. The adhesive material is for adhesively bonding the needle to the adjacent vertebral bodies. In some embodiments, a needle also has various surface contours along its shaft, including angled teeth and backfacing ridges.

6 Claims, 33 Drawing Sheets

U.S. PATENT DOCUMENTS

| | | | |
|---|---|---|---|
| 6,149,650 A | 11/2000 | Michelson | |
| RE37,005 E | 12/2000 | Michelson | |
| 6,159,215 A | 12/2000 | Urbahns et al. | |
| 6,190,388 B1 | 2/2001 | Michelson | |
| 6,210,412 B1 | 4/2001 | Michelson | |
| RE37,161 E | 5/2001 | Michelson | |
| 6,224,595 B1 | 5/2001 | Michelson | |
| 6,224,607 B1 | 5/2001 | Michelson | |
| 6,241,770 B1 | 6/2001 | Michelson | |
| 6,264,656 B1 | 7/2001 | Michelson | |
| 6,270,498 B1 | 8/2001 | Michelson | |
| 6,302,914 B1 | 10/2001 | Michelson | |
| 6,350,283 B1 | 2/2002 | Michelson | |
| 6,436,098 B1 | 8/2002 | Michelson | |
| 6,447,544 B1 | 9/2002 | Michelson | |
| 6,447,547 B1 | 9/2002 | Michelson | |
| 6,478,823 B1 | 11/2002 | Michelson | |
| 6,485,517 B1 | 11/2002 | Michelson | |
| 6,500,205 B1 | 12/2002 | Michelson | |
| 6,537,320 B1 | 3/2003 | Michelson | |
| 6,554,836 B2 | 4/2003 | Michelson | |
| 6,558,423 B1 * | 5/2003 | Michelson | 623/17.11 |
| 6,565,574 B2 | 5/2003 | Michelson | |
| 6,582,432 B1 | 6/2003 | Michelson | |
| 6,605,089 B1 | 8/2003 | Michelson | |
| 6,652,584 B2 | 11/2003 | Michelson | |
| 6,666,890 B2 | 12/2003 | Michelson | |
| 6,709,458 B2 | 3/2004 | Michelson | |
| 6,716,247 B2 | 4/2004 | Michelson | |
| 6,730,127 B2 | 5/2004 | Michelson | |
| 6,733,535 B2 | 5/2004 | Michelson | |
| 6,749,636 B2 | 6/2004 | Michelson | |
| 6,758,849 B1 | 7/2004 | Michelson | |
| 6,767,367 B1 | 7/2004 | Michelson | |
| 6,770,074 B2 | 8/2004 | Michelson | |
| 6,793,679 B2 | 9/2004 | Michelson | |
| 6,808,537 B2 | 10/2004 | Michelson | |
| 6,814,756 B1 | 11/2004 | Michelson | |
| 6,827,740 B1 | 12/2004 | Michelson | |
| 6,849,093 B2 | 2/2005 | Michelson | |
| 6,875,213 B2 | 4/2005 | Michelson | |
| 6,890,355 B2 | 5/2005 | Michelson | |
| 6,923,810 B1 | 8/2005 | Michelson | |
| 6,923,830 B2 | 8/2005 | Michelson | |
| 6,962,606 B2 | 11/2005 | Michelson | |
| 6,972,019 B2 | 12/2005 | Michelson | |
| 6,972,035 B2 | 12/2005 | Michelson | |
| 6,981,975 B2 | 1/2006 | Michelson | |
| 6,989,031 B2 | 1/2006 | Michelson | |
| 7,008,453 B1 | 3/2006 | Michelson | |
| 7,022,137 B2 | 4/2006 | Michelson | |
| 7,033,394 B2 | 4/2006 | Michelson | |
| 7,041,135 B2 | 5/2006 | Michelson | |
| 7,051,417 B2 | 5/2006 | Michelson | |
| 7,056,342 B2 | 6/2006 | Michelson | |
| 7,063,701 B2 | 6/2006 | Michelson | |
| 7,063,702 B2 | 6/2006 | Michelson | |
| 7,066,961 B2 | 6/2006 | Michelson | |
| 7,094,239 B1 | 8/2006 | Michelson | |
| 7,112,206 B2 | 9/2006 | Michelson | |
| 7,115,128 B2 | 10/2006 | Michelson | |
| 7,115,143 B1 | 10/2006 | Michelson | |
| 7,118,579 B2 | 10/2006 | Michelson | |
| 7,118,598 B2 | 10/2006 | Michelson | |
| 7,128,760 B2 | 10/2006 | Michelson | |
| 7,156,875 B2 | 1/2007 | Michelson | |
| 7,163,561 B2 | 1/2007 | Michelson | |
| 7,166,107 B2 | 1/2007 | Anderson | |
| 7,166,129 B2 | 1/2007 | Michelson | |
| 7,207,991 B2 | 4/2007 | Michelson | |
| 7,244,275 B2 | 7/2007 | Michelson | |
| 7,255,698 B2 | 8/2007 | Michelson | |
| 7,264,622 B2 | 9/2007 | Michelson | |
| 7,288,093 B2 | 10/2007 | Michelson | |
| 7,291,149 B1 | 11/2007 | Michelson | |
| 7,320,686 B2 | 1/2008 | Serhan et al. | |
| 7,326,214 B2 | 2/2008 | Michelson | |
| 7,326,248 B2 | 2/2008 | Michelson | |
| 7,354,442 B2 | 4/2008 | Sasso et al. | |
| 7,387,643 B2 | 6/2008 | Michelson | |
| 7,396,365 B2 | 7/2008 | Michelson | |
| 7,399,303 B2 | 7/2008 | Michelson | |
| 7,410,501 B2 | 8/2008 | Michelson | |
| 7,431,722 B1 | 10/2008 | Michelson | |
| 7,435,262 B2 | 10/2008 | Michelson | |
| 7,442,209 B2 | 10/2008 | Michelson | |
| 7,445,636 B2 | 11/2008 | Michelson | |
| 7,452,359 B1 | 11/2008 | Michelson | |
| 7,455,672 B2 | 11/2008 | Michelson | |
| 7,455,692 B2 | 11/2008 | Michelson | |
| 7,462,195 B1 | 12/2008 | Michelson | |
| 7,491,205 B1 | 2/2009 | Michelson | |
| 7,503,933 B2 | 3/2009 | Michelson | |
| 7,534,254 B1 | 5/2009 | Michelson | |
| 7,540,882 B2 | 6/2009 | Michelson | |
| 7,569,054 B2 | 8/2009 | Michelson | |
| 7,608,107 B2 | 10/2009 | Michelson | |
| 7,611,536 B2 | 11/2009 | Michelson | |
| 7,618,423 B1 | 11/2009 | Valentine et al. | |
| 7,637,951 B2 | 12/2009 | Michelson | |
| 7,637,954 B2 | 12/2009 | Michelson | |
| 7,655,027 B2 | 2/2010 | Michelson | |
| 7,686,805 B2 | 3/2010 | Michelson | |
| 7,691,148 B2 | 4/2010 | Michelson | |
| 7,722,619 B2 | 5/2010 | Michelson | |
| 7,771,475 B2 | 8/2010 | Michelson | |
| 7,789,914 B2 | 9/2010 | Michelson | |
| 7,794,502 B2 | 9/2010 | Michelson | |
| 7,828,800 B2 | 11/2010 | Michelson | |
| 7,887,565 B2 | 2/2011 | Michelson | |
| 7,892,286 B2 | 2/2011 | Michelson | |
| 7,914,530 B2 | 3/2011 | Michelson | |
| 7,914,554 B2 | 3/2011 | Michelson | |
| 7,922,729 B2 | 4/2011 | Michelson | |
| 7,931,840 B2 | 4/2011 | Michelson | |
| 7,935,116 B2 | 5/2011 | Michelson | |
| 7,935,149 B2 | 5/2011 | Michelson | |
| 7,942,933 B2 | 5/2011 | Michelson | |
| 7,972,365 B2 | 7/2011 | Michelson | |
| 7,972,381 B2 | 7/2011 | Michelson | |
| 7,976,566 B2 | 7/2011 | Michelson | |
| 2002/0099378 A1 | 7/2002 | Michelson | |
| 2003/0191371 A1 | 10/2003 | Smith et al. | |
| 2005/0137707 A1 * | 6/2005 | Malek | 623/17.12 |
| 2007/0225813 A1 | 9/2007 | Haines | |
| 2008/0281428 A1 * | 11/2008 | Meyers et al. | 623/20.35 |
| 2009/0149959 A1 * | 6/2009 | Conner et al. | 623/17.16 |
| 2010/0114317 A1 | 5/2010 | Lambrecht et al. | |

FOREIGN PATENT DOCUMENTS

RU        2004218 C1 * 12/1993

OTHER PUBLICATIONS

U.S. Appl. No. 60/989,100, filed Nov. 19, 2007.*
U.S. Appl. No. 12/361,525, filed Jan. 28, 2009, Wensel, Jeffrey Paris.
U.S. Appl. No. 12/383,950, filed Mar. 27, 2009, Wensel, Jeffrey Paris.
U.S. Appl. No. 12/705,970, filed Feb. 15, 2010, Wensel, Jeffrey Paris.
U.S. Appl. No. 12/705,972, filed Feb. 15, 2010, Wensel, Jeffrey Paris.
U.S. Appl. No. 12/705,974, filed Feb. 15, 2010, Wensel, Jeffrey Paris.
U.S. Appl. No. 12/705,978, filed Feb. 15, 2010, Wensel, Jeffrey Paris.
U.S. Appl. No. 13/032,634, filed Feb. 22, 2011, Wensel, Jeffrey Paris.
Portions of prosecution history of U.S. Appl. No. 12/361,525, Jul. 8, 2011, Wensel, Jeffrey Paris.
Portions of prosecution history of U.S. Appl. No. 12/383,950, Jul. 21, 2011, Wensel, Jeffrey Paris.
Portions of prosecution history of U.S. Appl. No. 12/705,970, Jul. 27, 2010, Wensel, Jeffrey Paris.
Portions of prosecution history of U.S. Appl. No. 12/705,972, Jul. 27, 2010, Wensel, Jeffrey Paris.
Portions of prosecution history of U.S. Appl. No. 12/705,974, Jul. 27, 2010, Wensel, Jeffrey Paris.
Portions of prosecution history of U.S. Appl. No. 12/705,978, Jul. 27, 2010, Wensel, Jeffrey Paris.
Updated portions of prosecution history of U.S. Appl. No. 12/361,525, Oct. 4, 2011, Wensel, Jeffrey Paris.

Updated portions of prosecution history of U.S. Appl. No. 12/383,950, Oct. 28, 2011, Wensel, Jeffrey Paris.
Updated portions of prosecution history of U.S. Appl. No. 12/361,525, Jun. 14, 2012, Wensel, Jeffrey Paris.
Updated portions of prosecution history of U.S. Appl. No. 12/705,972, May 14, 2012, Wensel, Jeffrey Paris.
Updated portions of prosecution history of U.S. Appl. No. 12/361,525, Feb. 14, 2012, Wensel, Jeffrey Paris.
Updated portions of prosecution history of U.S. Appl. No. 12/705,970, Mar. 22, 2012, Wensel, Jeffrey Paris.
Updated portions of prosecution history of U.S. Appl. No. 12/705,972, Apr. 12, 2012, Wensel, Jeffrey Paris.
Updated portions of prosecution history of U.S. Appl. No. 12/705,978, Mar. 22, 2012, Wensel, Jeffrey Paris.
Updated portions of prosecution history of U.S. Appl. No. 12/383,950, Jun. 20, 2012, Wensel, Jeffrey Paris.
Updated portions of prosecution history of U.S. Appl. No. 12/705,974, Jun. 19, 2012, Wensel, Jeffrey Paris.

* cited by examiner

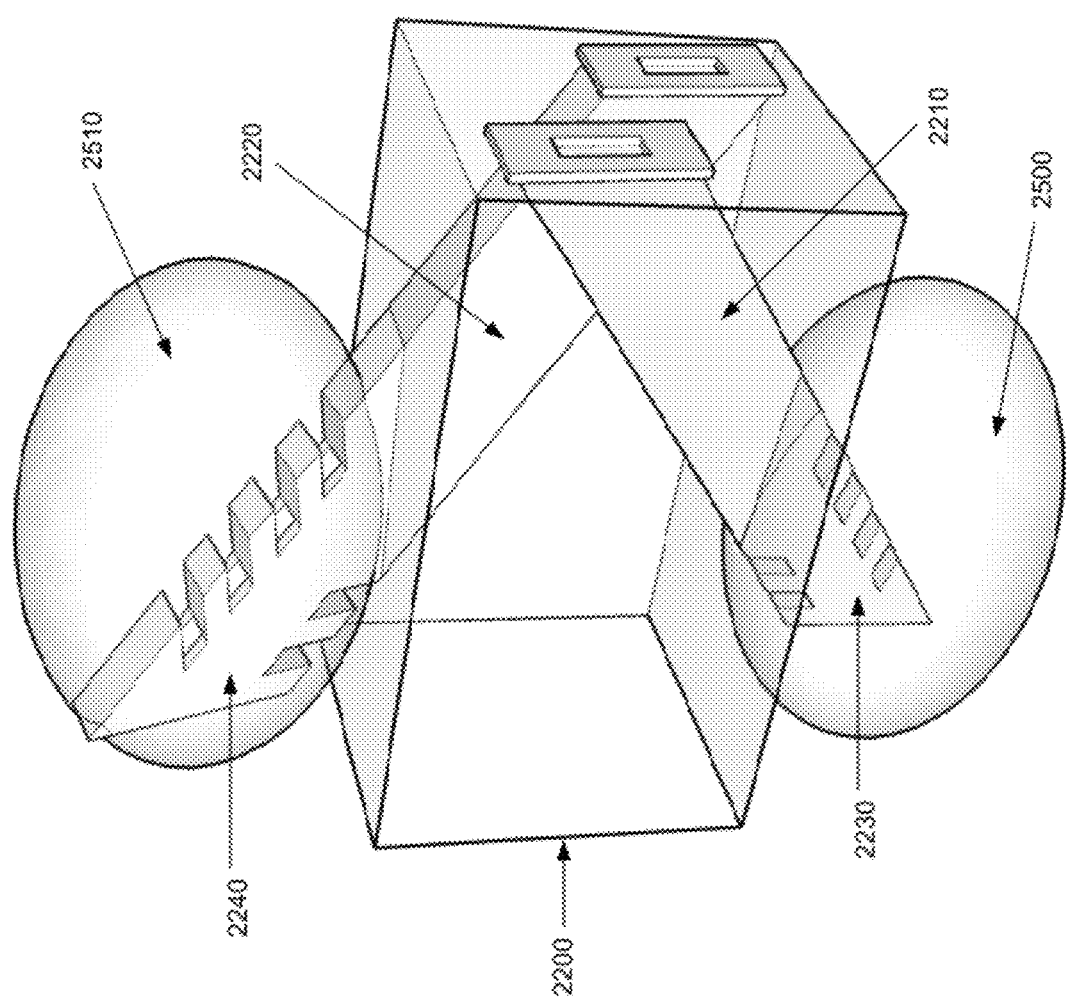

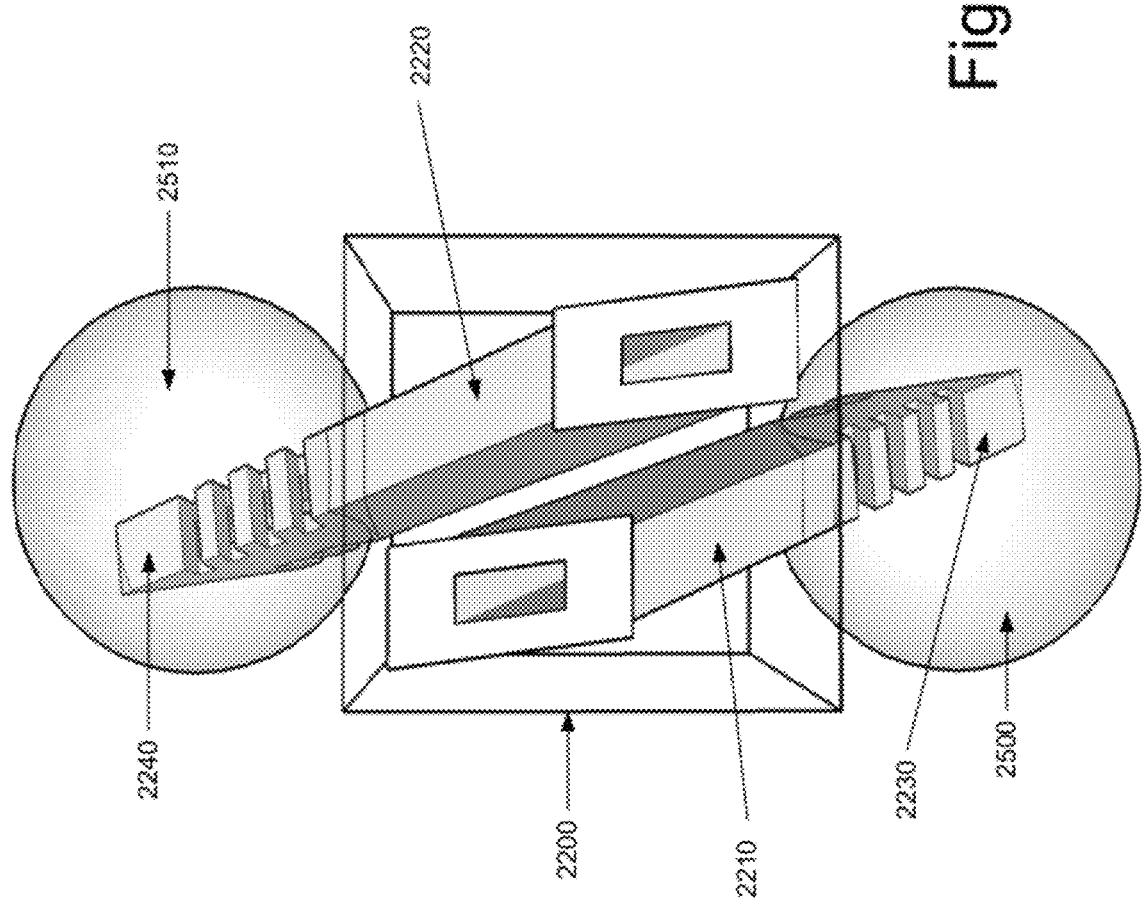

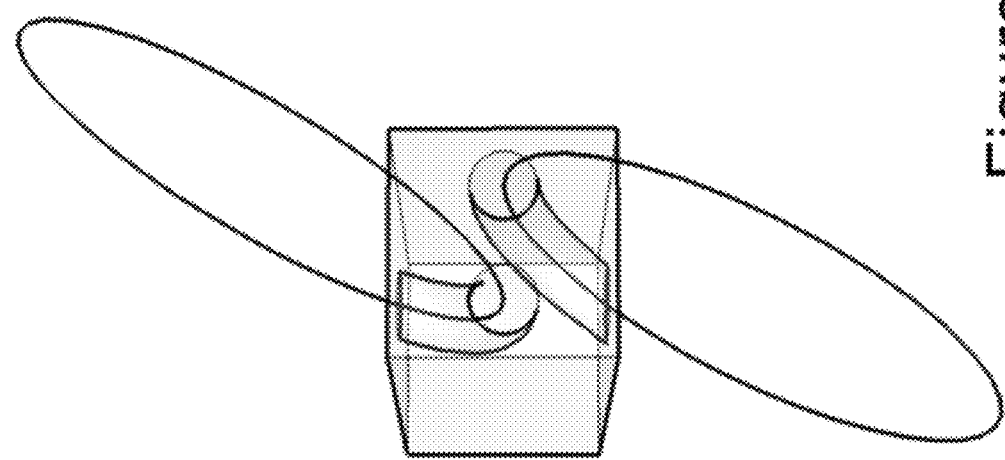
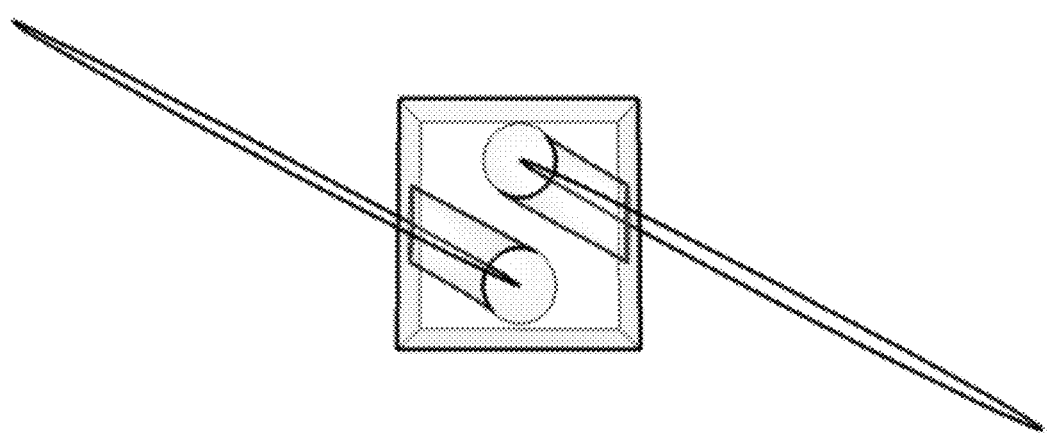
Figure 27B

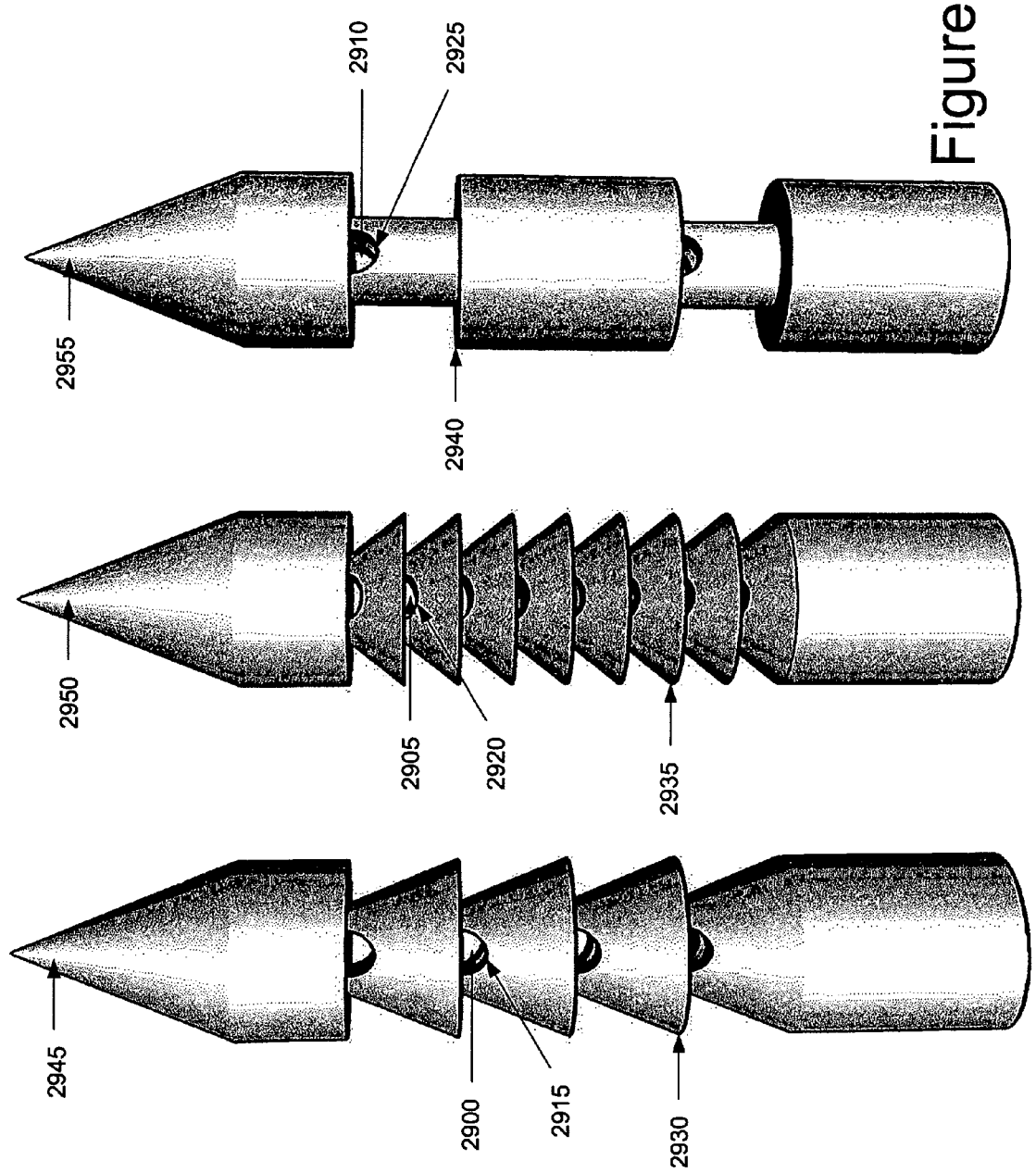

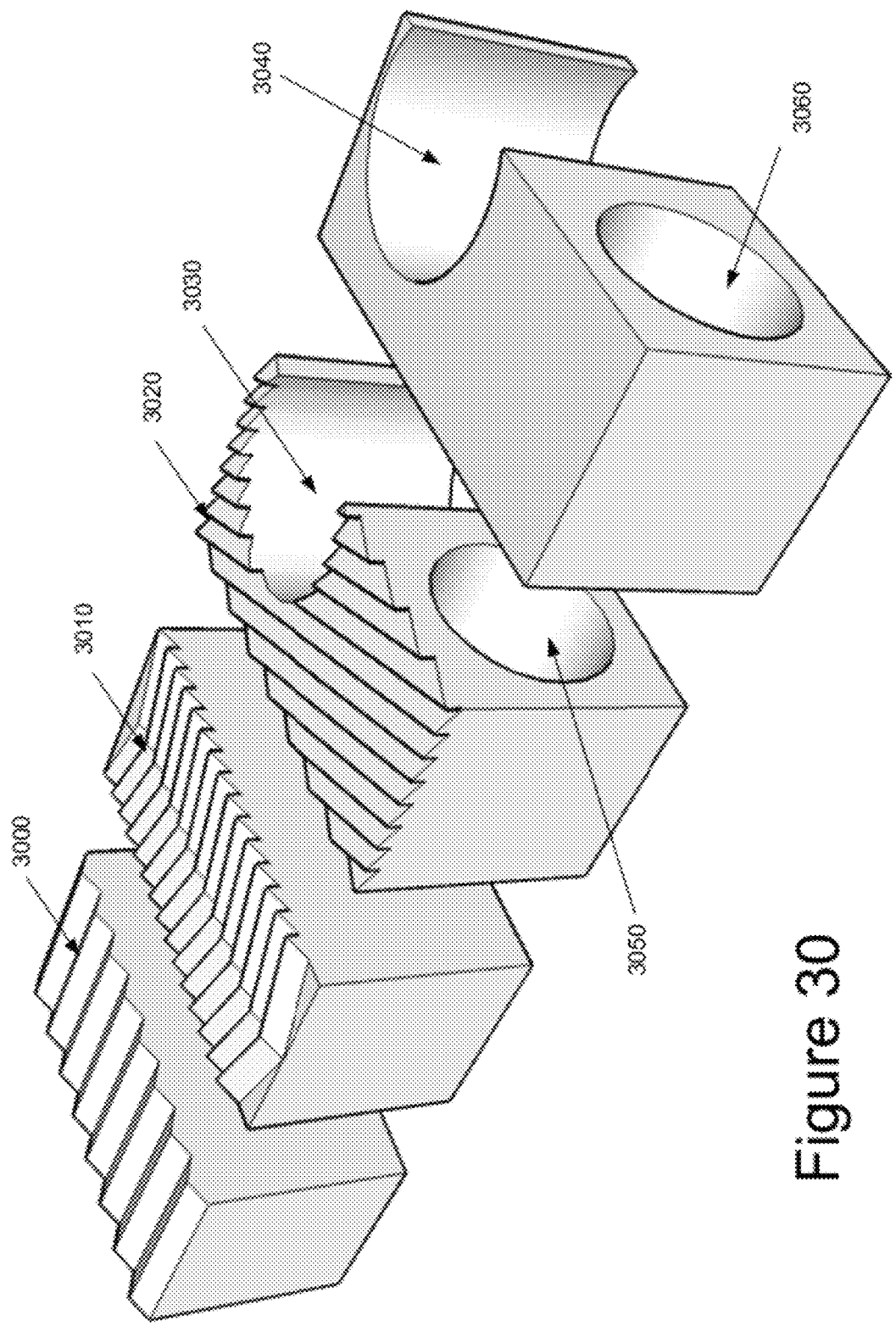

INTERVERTEBRAL FUSION DEVICE AND METHOD OF USE

This Application claims benefit to U.S. Provisional Patent Application 61/040,136, entitled "Intervertebral Fusion Device and Method of Use", filed Mar. 27, 2008.

FIELD OF THE INVENTION

The invention pertains to spinal implants and surgical procedures for spinal fusion and stabilization.

BACKGROUND OF THE INVENTION

Back and neck pain are the leading causes of disability and lost productivity for American workers under the age of 45. Degenerative disc disease and its sequelae, whereby the fibrocartilaginous disc between adjacent vertebral bodies loses height, hydration and structural integrity, is one of the most common causes of back and neck pain and may develop secondary to traumatic injuries, inflammatory processes or various degenerative disorders. When conservative treatment fails, surgical fusion of the vertebral segments across the abnormal disc may be the only currently available procedure for pain relief. An increasing number of these spinal fusions are performed each year. It is estimated that over half a million of these procedures were performed in the United States last year alone.

Various surgical approaches to abnormal lumbar disc spaces are employed and include anterior interbody fusions, posterior interbody fusions and tranforaminal fusions. At cervical levels, an anterior approach is employed. These procedures may be augmented by various posterior element instrumentation techniques. Regardless of the surgical approach, the goal is to achieve solid bony fusion between the involved endplates and eliminate the symptoms caused by motion and associated degenerative and other reactive changes between these unstable vertebral segments.

The first lumbar fusion procedures involved removal of a portion of the abnormal disc and placement of autologous bone graft material in the disc space without instrumentation of posterior elements. This approach often failed due to inadequate structural integrity. Subsequently, cortical bone dowels and femoral ring allografts were employed in an attempt to restore disc space height and augment structural integrity. After U.S. Pat. No. 4,961,740 ("Ray, et al.") introduced the concept of the threaded cylindrical interbody fusion cage in 1990, numerous other interbody fusion devices were developed. These devices include cylindrical, rectangular, and tapered cages and spacers composed of metals, polymers, human bone allograft and other materials. Some of these devices incorporate or are coated with human bone morphogenetic protein or other agents to promote new bone formation and accelerate fusion. Despite these advancements, failure rates for spinal fusion surgeries remain unacceptably high, greater than 10 percent in most series.

Therefore, there is a need in the art for an improved method to effect a more rapid, reliable fusion between unstable vertebral segments and avoid the considerable medical and economic impact of failed spinal fusions.

SUMMARY OF THE INVENTION

Some embodiments of the invention disclose an apparatus for achieving rapid mechanical fusion between two vertebral bodies. In some embodiments, an interbody fusion member (e.g., a shaped block, such as a rectangular or oblong block) with one or more tubular channels is positioned between the endplates of adjacent vertebrae following partial or complete discectomy. In this position, two or more sides of the fusion member are in contact with the opposed endplates. These contacting sides may be parallel to each other, or nonparallel such that the fusion block presents a tapered profile when viewed laterally so as to restore both disc height and physiologic lordosis.

Once properly positioned, one or more needles (e.g., large gauge needles 1-10 mm in outer diameter) are passed through the fusion member's channels and advanced into the marrow space of the adjacent vertebral body. In some embodiments, a flange at the base of each needle fits into a recess of increased diameter where the tubular channel meets the exposed block surface locking the needle's position and anchoring it to the block. A needle is open or closed at its tip. Moreover, a needle may have perforations of various spacing and configuration along its shaft. In some embodiments, the needle's opening and/or perforations communicate directly with a central lumen, which extends to the needle base. In some embodiments, a needle also has various surface contours along its shaft, including angled teeth and backfacing ridges.

In some embodiments, the segments of the needles comprising these contours (e.g., angled teeth and backfacing ridges) have a diameter or circumference that is less than or equal to the diameter or circumference of proximal or distal needle segments. This allows the needle to pass through the fusion member's channel and into the bone readily (i.e., into the adjacent vertebral body).

Once a needle is in position, an adhesive may be injected through the needle. Examples of such an adhesive include any quickly hardening adhesives, such as polymethyl methacrylate (PMMA) or other bone cement or polymer. This material passes through the perforations and/or openings of the needle into the marrow space of the vertebral body, contiguous with or adjacent to the surface contours of the needle, including angled teeth and/or back facing ridges. The adhesive clouds in some embodiments form a spherical or ellipsoidal "cloud" of PMMA contiguous with the needle tip. Once the adhesive cloud hardens, the surface contours anchor the needle and prevent it from being withdrawn from the trabecular bone, and thereby enhances the structural integrity of the inserted fusion device. In some embodiments, more than one needle is advanced through multiple channels of a fusion member into the same vertebral body and adhesives (PMMA or other bone cement or polymer) are injected through these needles. The resultant PMMA clouds from adjacent needle tips or perforations may unite to form a single larger cloud upon polymerization. The united cloud along with multiple contoured and perforated needles locks the fusion member with the trabecular bone of the vertebral body. One or more additional needles may be passed through additional channels and into the marrow space of the vertebral body contiguous with the opposite face of the fusion member and the injection process repeated. The final result is an intervertebral fusion member anchored via multiple contoured, perforated needles to collections of adhesive clouds (e.g., PMMA clouds) and to the trabecular bone of adjacent vertebral bodies yielding solid mechanical fusion.

The fusion member may be composed of any number of materials, such as metals (including stainless steel, titanium, or nitinol), various polymers (including PMMA or polyetheretherketone), carbon fiber, etc. In some embodiments, the fusion member is partially or completely made of bioabsorbable or biodegradable materials, so that it can partially or completely be absorbed. In some instances, the fusion member's faces that are in contact with the vertebral endplates may have ridges or other surface contouring to enhance stability. The fusion member may comprise additional channels or cavities to be packed with bone graft material or bone graft substitutes to enhance progressive solid bony fusion. The fusion member may also be coated with or partially composed of human morphogenetic protein or other bone-inducing substances.

Like the fusion member, the needles that are inserted in it can be composed of many materials. Examples of such materials include nitinol, stainless steel, titanium or other metals or metallic alloys or of high density polymers, carbon fiber or of a combination of these materials.

BRIEF DESCRIPTION OF THE DRAWINGS

The novel features of the invention are set forth in the appended claims. However, for purpose of explanation, several embodiments of the invention are set forth in the following figures.

FIGS. 25 and 26 illustrate different views of PMMA that has been injected and forms collections contiguous with the perforated, contoured tips of needles within the marrow spaces of adjacent vertebral bodies.

FIGS. 27a, 27b, and 28 illustrate different views of an alternative fusion member embodiment comprising curved tubular channels that run in parallel planes with respect to each other but are nonparallel to the adjacent faces of the fusion block member.

FIGS. 29a and 29b illustrate alternative needle tips

FIG. 30 illustrates various block surface contour features.

DETAILED DESCRIPTION OF THE INVENTION

Figure 1:
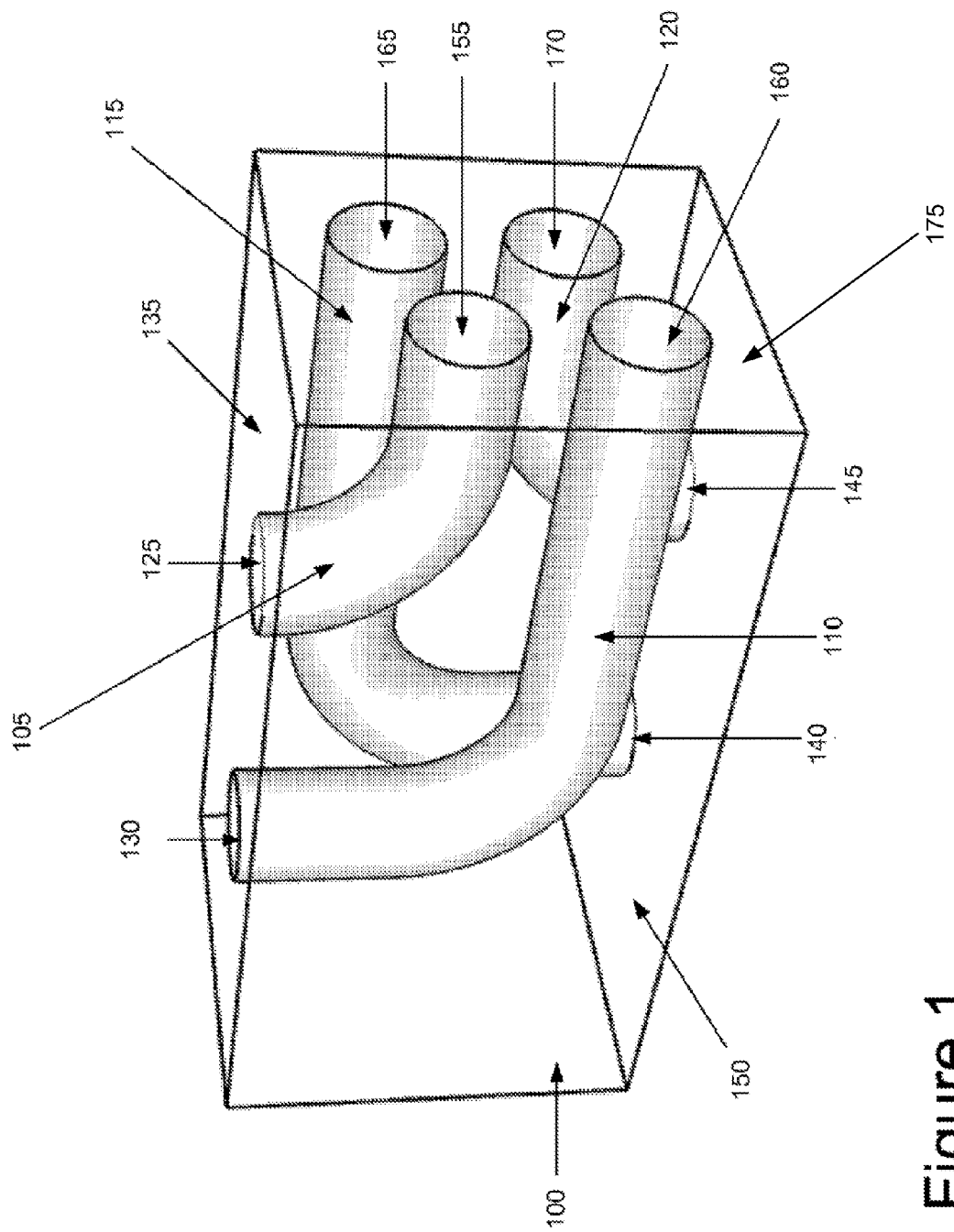
FIGS. 1-3 illustrate different views of an interbody fusion member comprising curved tubular channels with distal openings on the superior block face and inferior block face.

In the following description, numerous details are set forth to provide a better understanding of the various embodiments of the invention. However, one of reasonable skill in the art will realize that the invention may be practiced without the use of the specific details presented herein. In some instances of describing the invention, well-known structures may be omitted or shown in block diagram form to avoid obscuring the description of the invention with unnecessary detail. Therefore, the examples provided herein for description and clarification should not be interpreted as in anyway limiting the language of the claims.

I. OVERVIEW

Some embodiments of the invention provide an apparatus for achieving rapid mechanical fusion between adjacent vertebral bodies in a living organism. In some embodiments, an interbody fusion member (e.g., a shaped block, such as a rectangular or oblong block) with one or more tubular channels is positioned between the endplates of adjacent vertebrae following partial or complete discectomy. In this position, two or more sides of the fusion member are in contact with the opposed endplates. These contacting sides may be parallel to each other, or nonparallel such that the fusion block presents a tapered profile when viewed laterally so as to restore both disc height and physiologic lordosis.

Once properly positioned, one or more needles (e.g., large gauge needles 1-10 mm in outer diameter) are passed through the fusion member's channels and advanced into the marrow space of the adjacent vertebral body. In some embodiments, a flange at the base of each needle fits into a recess of increased diameter where the tubular channel meets the exposed block surface locking the needle's position and anchoring it to the block. In some embodiments, a smaller gauge needle is advanced into the marrow space of the adjacent vertebral body before placement of the large gauge needle. This creates a guide to help ensure the large gauge needle will be advanced into the proper position within the trabecular bone of the vertebral body. A needle may be open or closed at its tip. Moreover, a needle may have perforations of various spacing and configuration along its shaft. In some embodiments, the needle's opening and/or perforations communicate directly with a central lumen, which extends to the needle base. In some embodiments, a needle also has various surface contours along its shaft, including angled teeth and backfacing ridges.

In some embodiments, the segments of the needles comprising these contours (e.g., angled teeth and backfacing ridges) have a diameter or circumference that is less than or equal to the diameter or circumference of proximal or distal needle segments. This allows the needle to pass through the fusion member's channel and into the bone readily (i.e., into the adjacent vertebral body).

Once a needle is in position, an adhesive may be injected through the needle. Examples of such an adhesive include any quickly hardening adhesives, such as polymethyl methacrylate (PMMA) or other bone cement or polymer. This material passes through the perforations and/or openings of the needle into the marrow space of the vertebral body, contiguous with or adjacent to the surface contours of the needle, including angled teeth and back facing ridges. The adhesive clouds in some embodiments form a spherical or ellipsoidal "cloud" of PMMA contiguous with the needle tip. Once the adhesive cloud hardens, the surface contours anchor the needle and prevent it from being withdrawn from the trabecular bone, and thereby enhances the structural integrity of the inserted fusion device.

In some embodiments, more than one needle is advanced through multiple channels of a fusion member into the same vertebral body and adhesives (PMMA or other bone cement or polymer) are injected through these needles. The resultant PMMA clouds from adjacent needle tips or perforations may unite to form a single larger cloud upon polymerization. The united cloud along with multiple contoured and perforated needles locks the fusion member within the trabecular bone of the vertebral body. One or more additional needles may be passed through additional channels and into the marrow space of the vertebral body contiguous with the opposite face of the fusion member and the injection process repeated. The final result is an intervertebral fusion member anchored via multiple contoured, perforated needles to collections of hardened adhesive clouds (e.g., PMMA and other polymeric collections) and to the trabecular bone of adjacent vertebral bodies yielding solid mechanical fusion.

The fusion member may be composed of any number of materials, such as metals (including stainless steel, titanium, or nitinol), various polymers (including PMMA or polyetheretherketone), carbon fiber, etc. In some embodiments, the fusion member is partially or completely made of bioabsorbable or biodegradable materials, so that it can partially or completely be absorbed. In some instances, the fusion member's faces that are in contact with the vertebral endplates may have ridges or other surface contouring to enhance stability. The fusion member may comprise additional channels or cavities to be packed with bone graft material or bone graft substitutes to enhance progressive solid bony fusion. The fusion member may also be coated with or partially composed of human morphogenetic protein or other bone-inducing substances.

Like the fusion member, the needles that passed through its channels can be composed of many materials. Examples of such materials include nitinol, stainless steel, titanium or other metals or metallic alloys or of high density polymers, carbon fiber or of a combination of these materials.

To better understand these embodiments, it is helpful to understand relevant terminology and describe an example of the invention in use. Therefore, the following sections present relevant terminology, and provide an overview of an exemplary fusion procedure of some embodiments and of a number of specific design features and variations.

II. DEFINITIONS AND TERMINOLOGY

The spinal column of humans and other vertebrates comprises vertebral bodies and posterior osseous elements that provide structural support and also serve to protect the spinal cord and other spinal canal contents. The vertebral bodies are the cylindrical segmental osseous structures that form the anterior margin of the spinal canal and are separated from each other by fibrocartilaginous intervertebral discs. In the present discussion, the term "fusion member" refers to a device positioned between vertebral bodies. In some embodiments, the fusion member has one or more channels for the passage of contoured fusion needles and/or the retention and positioning of bone graft material or bone graft substitutes between adjacent vertebral bodies.

III. EXAMPLES OF FUSION MEMBERS AND NEEDLES

Some embodiments of the invention have particular utility when placed between the endplates of adjacent vertebral bodies following discectomy to effect a rapid mechanical fusion of adjacent vertebral segments.

Figure 2:
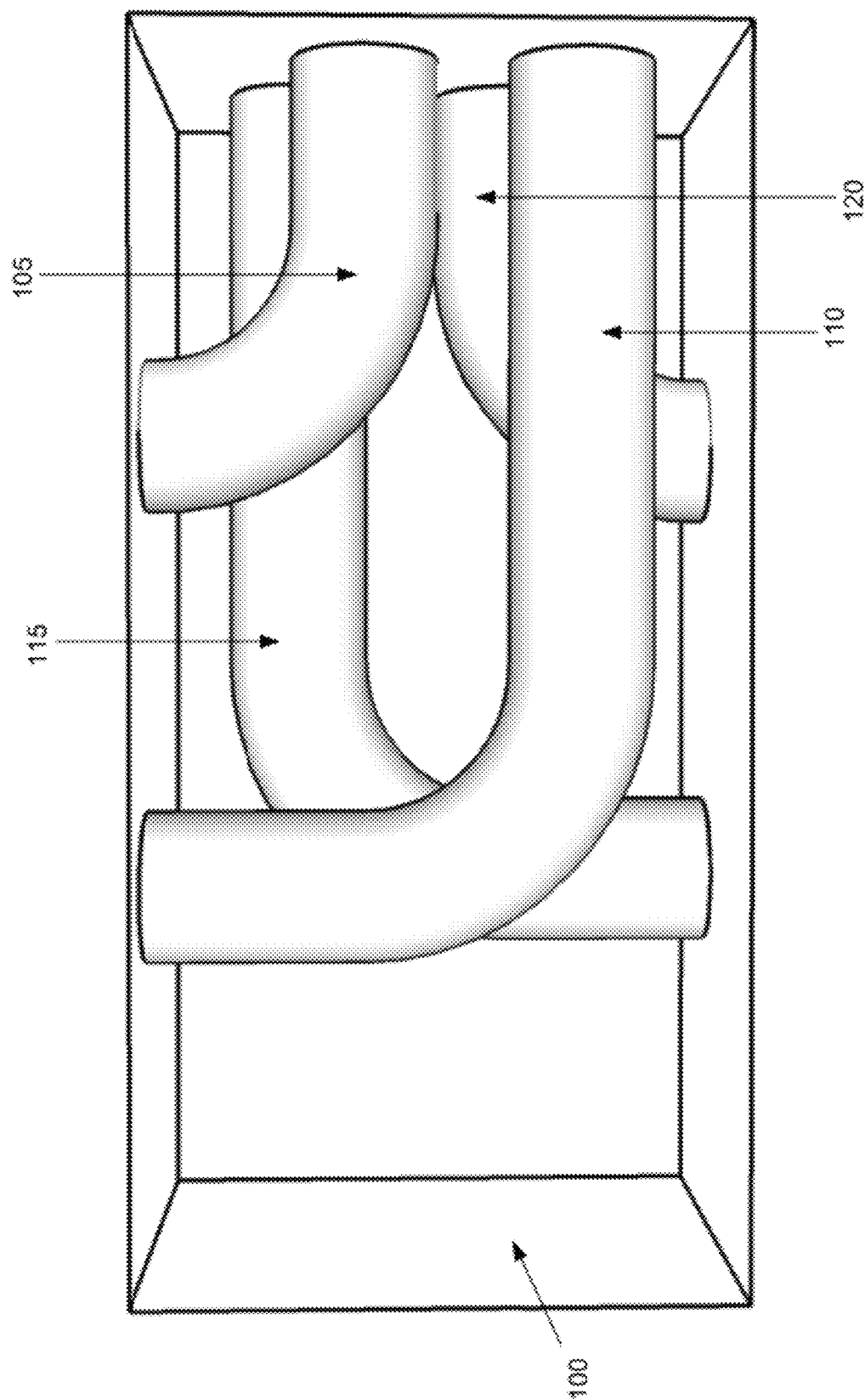
Figure 3:
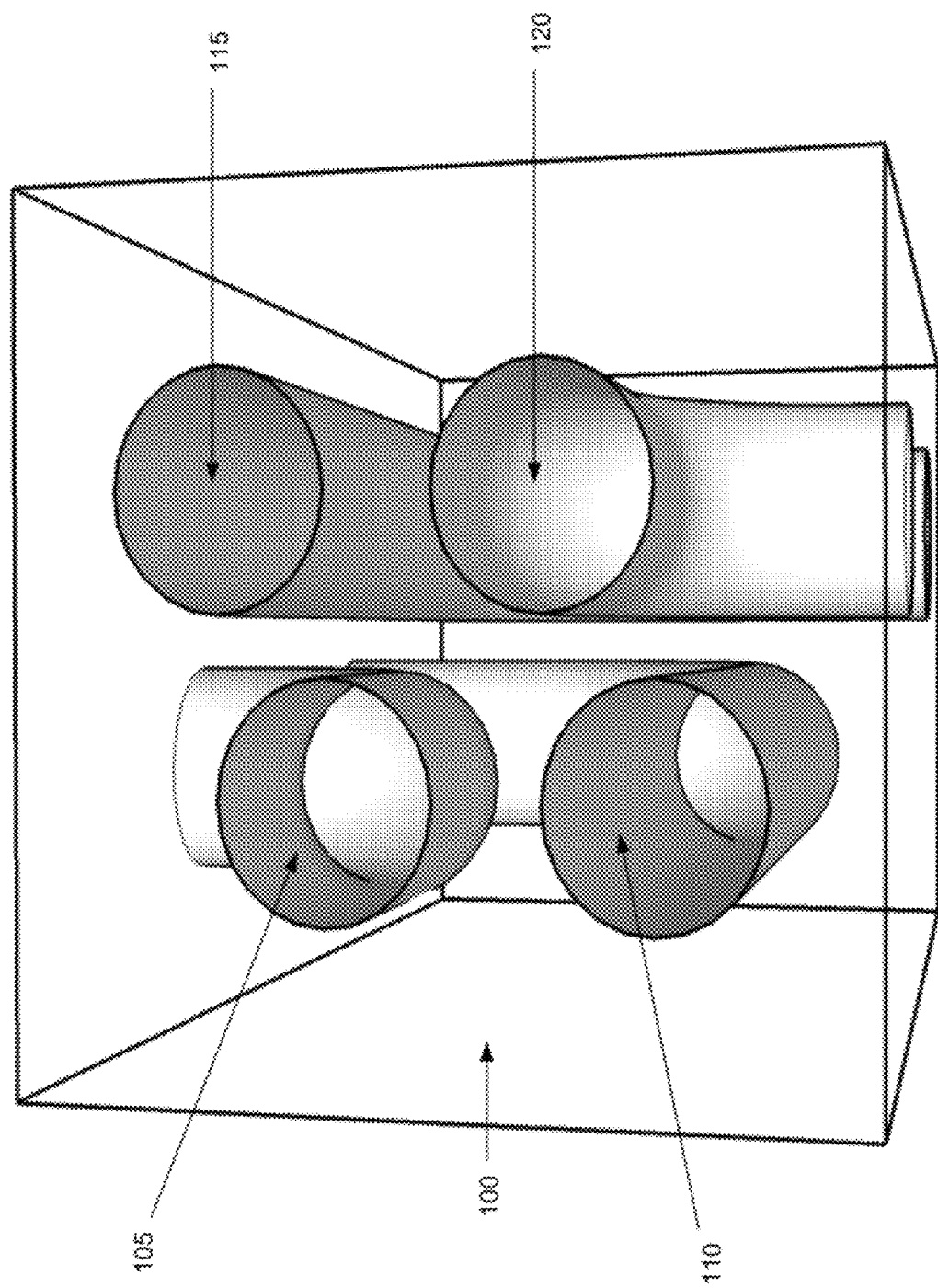

FIGS. 1, 2 and 3 illustrate different views of an interbody fusion member of some embodiments of the invention. As shown in these figures, the fusion member is a rectangular block 100. This block is inserted between two vertebral bodies after an incision is made in a patient and the disc between these two bodies is removed.

As shown in FIGS. 1, 2, and 3, the fusion block 100 includes (1) curved tubular channels 105 and 110, each with a distal opening 125 and 130 on the superior block face 135, and (2) curved tubular channels 115 and 120, each with a distal opening 140 and 145 on the inferior block face 150 (in these and subsequent figures, blocks are shown as transparent to facilitate an appreciation of the spatial relationships between multiple channels and their openings upon multiple block faces.) Each tubular channel also has a proximal opening 155, 160, 165, and 170 on the face 175 of the block through which the needles are introduced and advanced.

The superior block face 135 will abut one vertebrae, while the inferior block face 150 will abut the other vertebrae between which the block is placed. As further described below, large gauge needles (e.g., 1-10 mm in outer diameter) are passed through the proximal openings 155, 160, 165, and 170 on the face 175 of the block that are closest to the operator, and pass through the tubular channels 105, 110, 115, and 120, out of the distal openings 125, 130, 140, and 145 and into the trabecular bone of the vertebral bodies.

Figure 4:
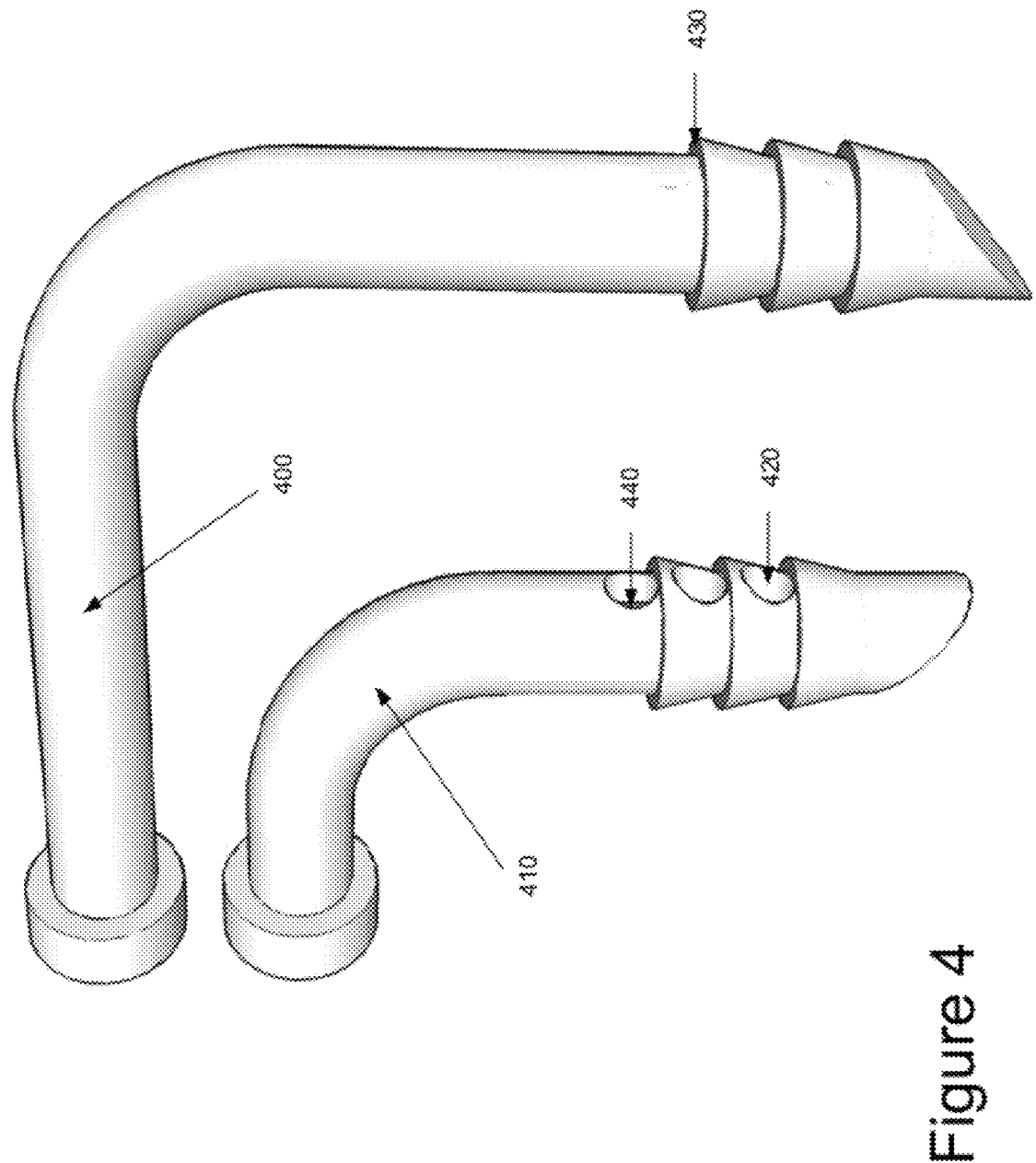
FIGS. 4 and 5 illustrate different views of flexible contoured hollow needles.
Figure 5:
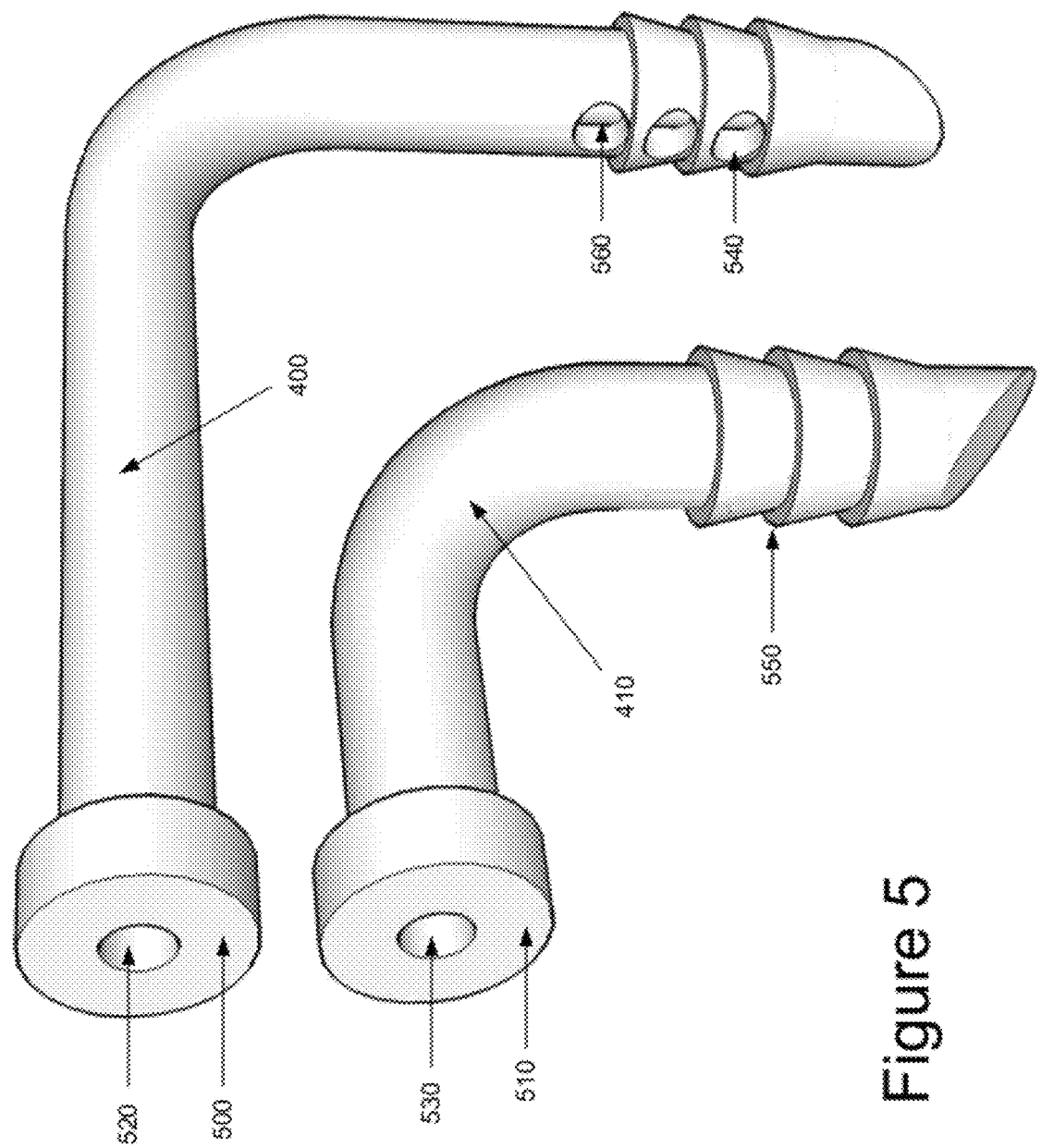

Examples of such needles are illustrated in FIGS. 4 and 5. These figures depict flexible contoured hollow needles 400 and 410. Each of these needles has several (e.g., three) distal perforations 420 or 540, a central lumen 440 or 560, and a flanged base 500 or 510. In each needle, the distal perforations 420 or 540 communicate with the needles' central lumen 440 or 560, which extends from the perforations to the flanged needle base 500 or 510 with an opening 520 or 530. Adhesive material can be injected into the opening 520 or 530, through the lumen 440 or 560 and out of the perforations 420 or 540 in order to deliver adhesive to the area immediately adjacent to the angled teeth, backfacing ridges, or other surface contours. As shown in FIGS. 4 and 5, the needles in some embodiments have back-facing retention ridges 430 or 550 along their distal shafts. As further described below, these ridges assist in the retention of the needle in the vertebral bodies and thereby further solidify the anchoring of the block 100 between the vertebral bodies.

Figure 6:
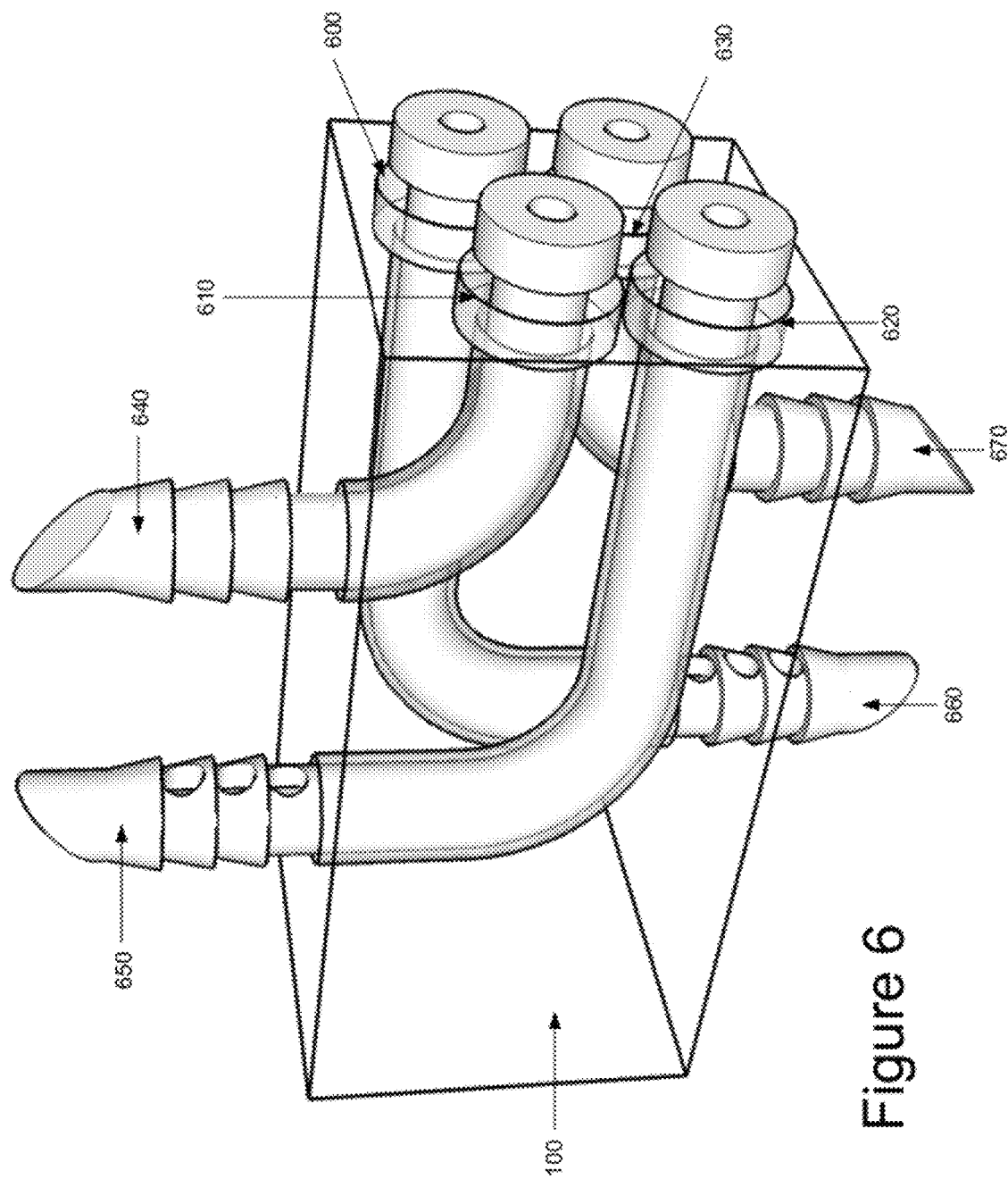
FIGS. 6 and 7 illustrate different views of needles that have been advanced through the fusion member channels after discectomy and following positioning of the fusion member between adjacent vertebrae.
Figure 7:
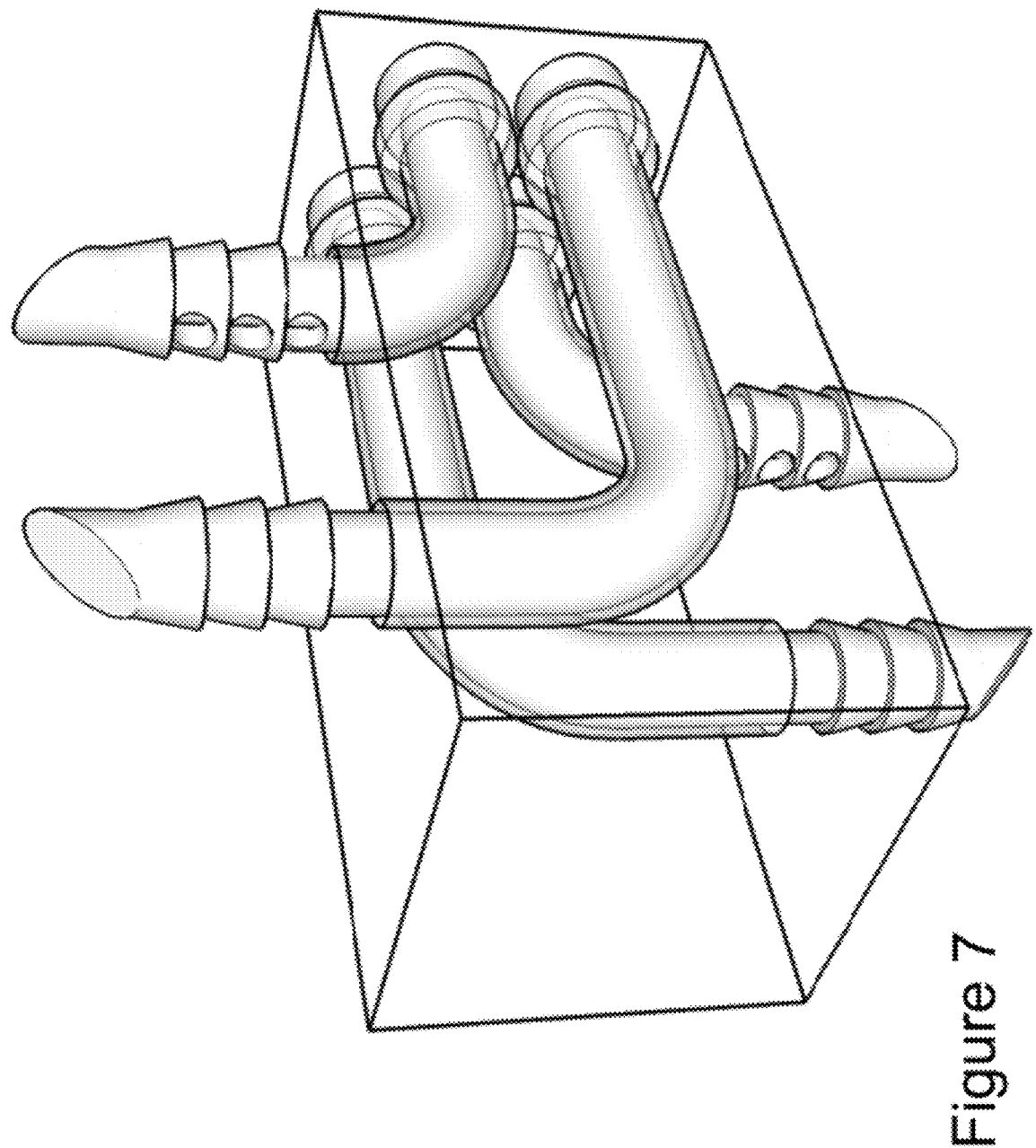

The use of the fusion block 100 and the needles will now be further described by reference to FIGS. 6-10. FIGS. 6 and 7 depict four needles 640, 650, 660, and 670 after they have been almost completely advanced through the fusion block's channels following a discectomy (i.e., the surgical removal of at least a portion of the fibrocartilaginous disc between two adjacent vertebrae) and the positioning of the block 100 between adjacent vertebrae (not pictured). A recess 600, 610, 620, and 630 at the proximal end of each tubular channel anchors each needle to the block when the needle is fully advanced.

Figure 8:
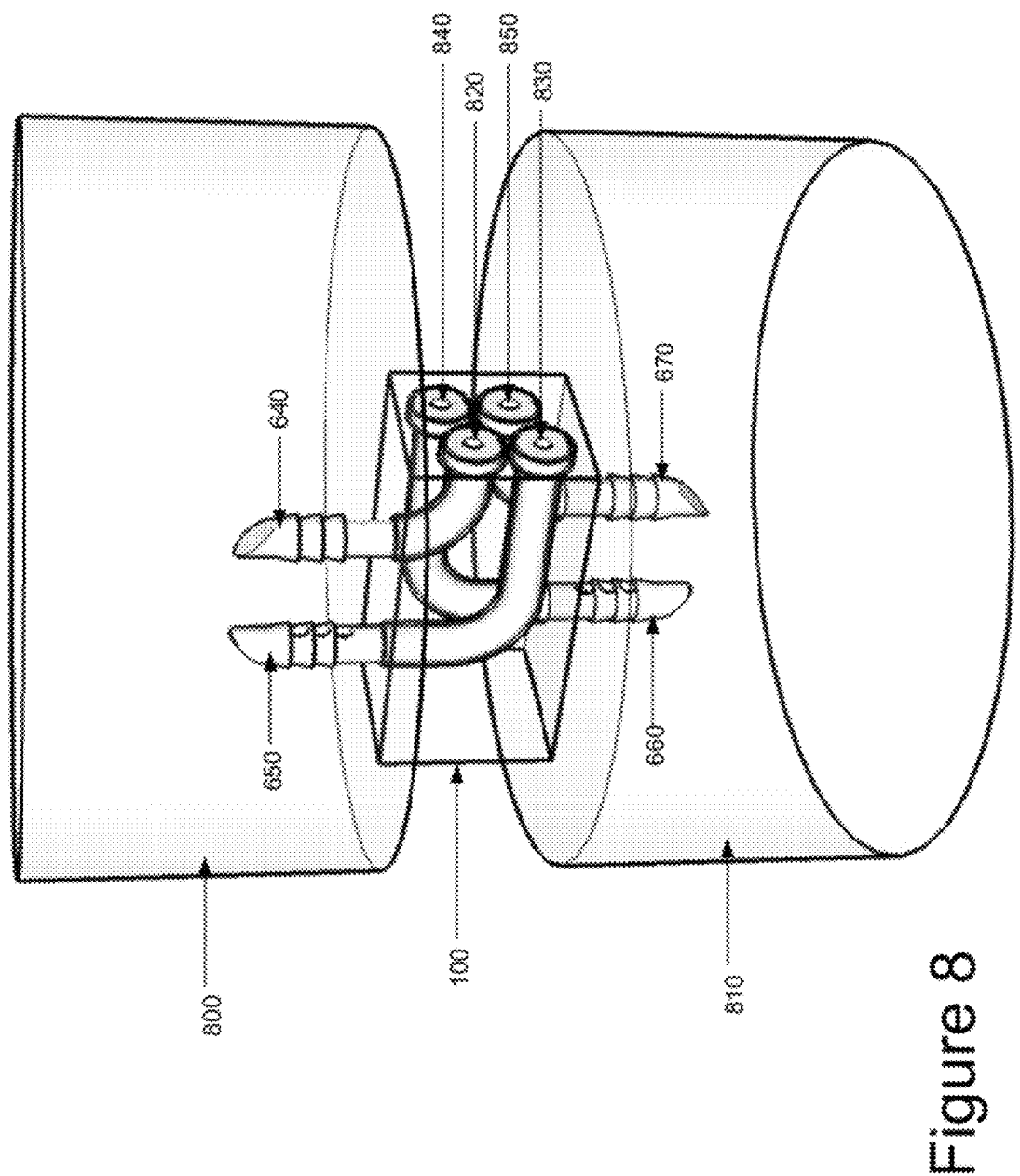
FIG. 8 illustrates needles that have been fully advanced through the fusion member channels into the marrow space of the adjacent vertebral bodies.

FIG. 8 illustrates two fusion needles 640 and 650 that have been fully advanced into the marrow space of the vertebral body 800 immediately above the fusion member and two fusion needles 660 and 670 have been advanced into the marrow space of the vertebral body 810 immediately beneath the fusion member.

Figure 9:
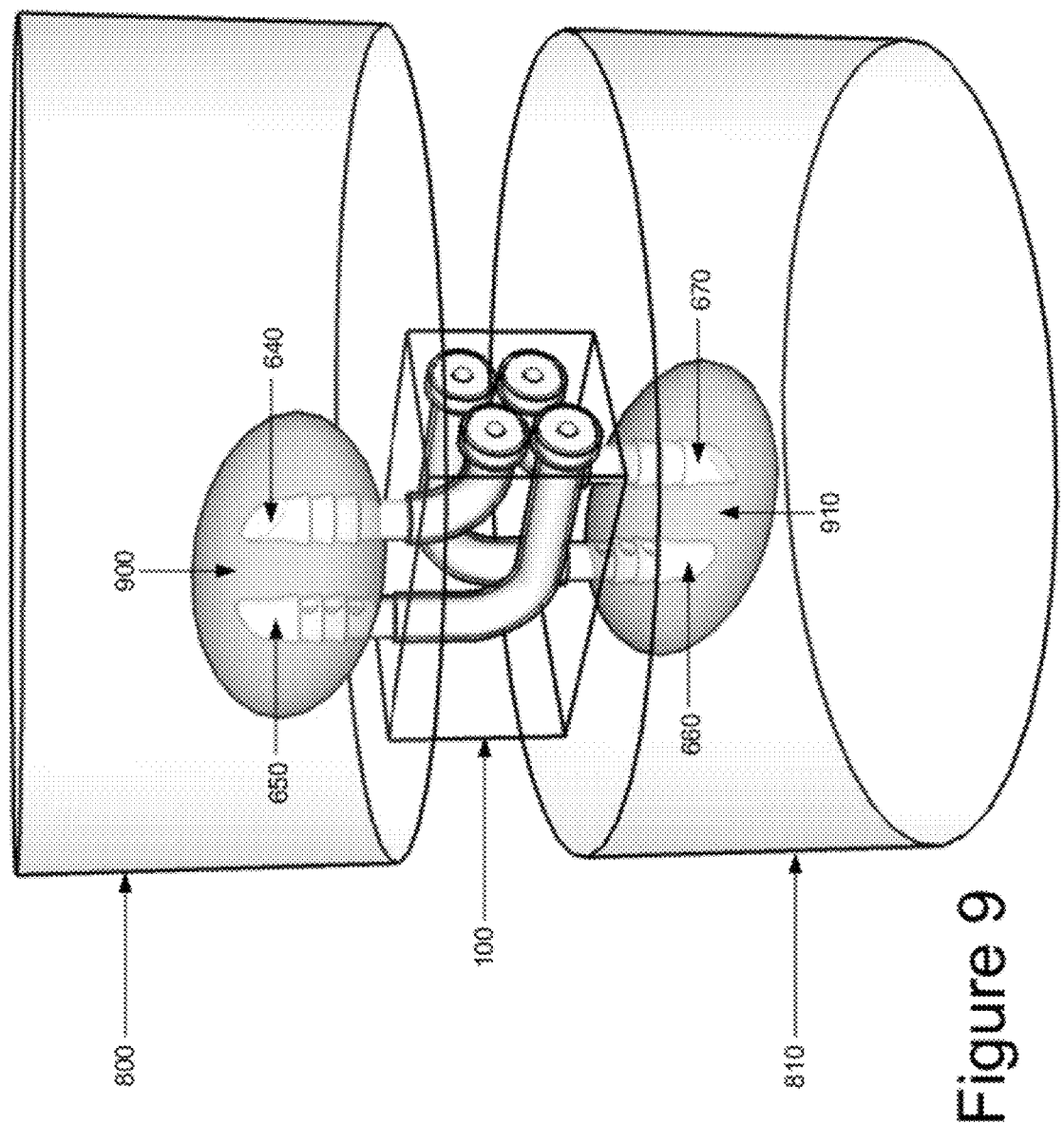
FIGS. 9 and 10 illustrate the coalescence of the PMMA collections that result following injections of PMMA through the needles into the marrow space of the adjacent vertebral bodies.

Once these needles are advanced into the vertebral bodies, adhesive material is injected through their openings 820, 830, 840, and 850, through their central lumens, and out of their perforations in order to deliver adhesive to the area immediately adjacent to their angled, backfacing ridges, or other surface contours in the vertebral bodies. FIG. 9 depicts the coalescence of the PMMA collections 900 and 910 that result following injections of PMMA via needles 640 and 650 and needles 660 and 670, respectively. Within minutes after injection, the PMMA polymerizes and hardens within the marrow space adjacent to and between the contoured needle tips, anchoring each vertebral body to the fusion assembly.

Figure 10:
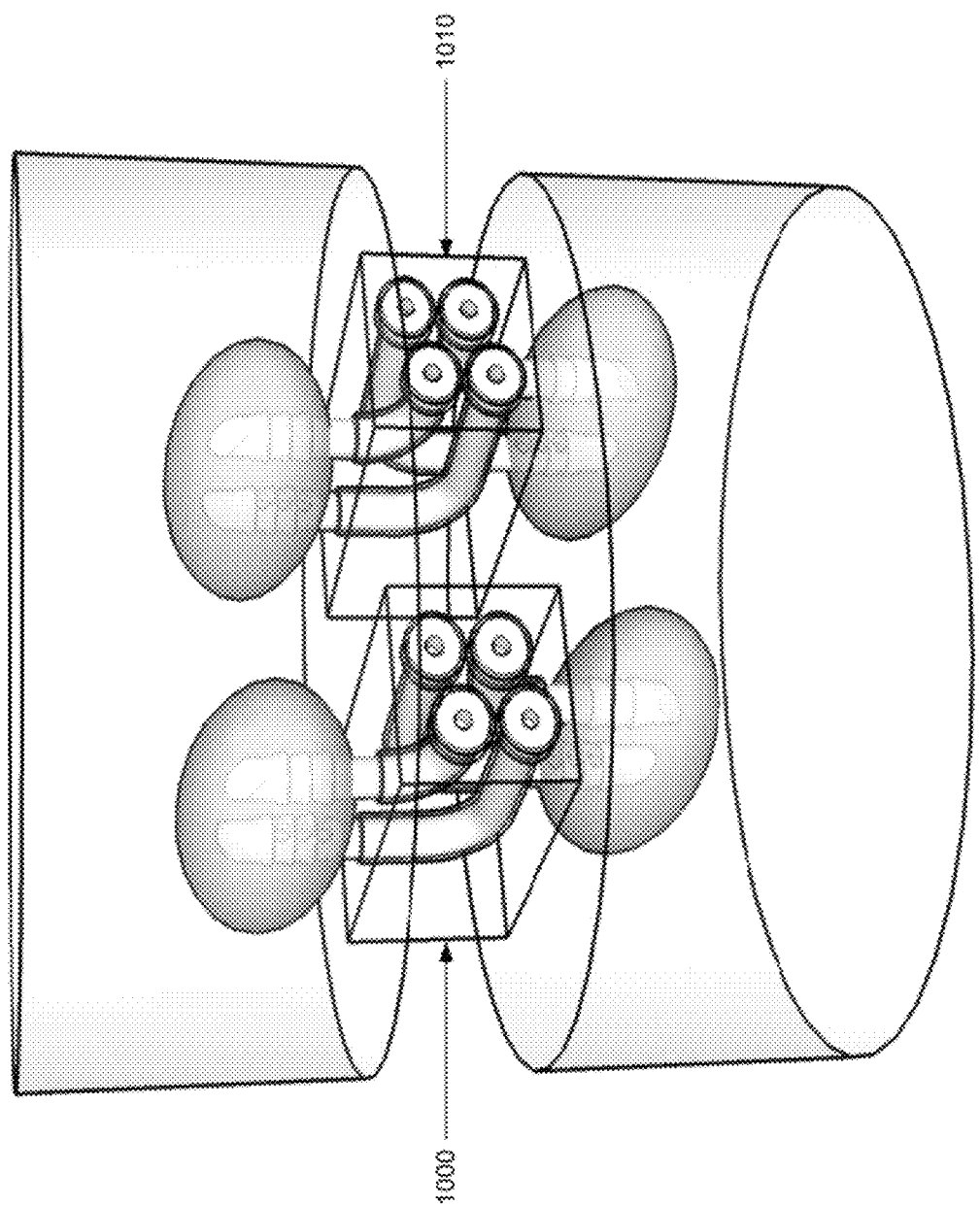

Some embodiments insert more than one fusion member between a pair of adjacent vertebral bodies. One such example is illustrated in FIG. 10. This figure depicts placement of two fusion members 1000 and 1010 within the right and left paramedian disc space, the placement of multiple sets of needles through two fusion members and into the vertebral bodies, and confluence of bilateral paramedian PMMA "clouds" following the PMMA injections. Bone graft material or bone graft substitutes may be packed into additional channels within the fusion members or into the intervertebral space surrounding and between the blocks to accelerate progressive solid bony fusion.

IV. ALTERNATIVE SHAPES

The shape and composition of the fusion members and needles are different in different embodiments.

A. Arc Shaped Channels and Needles

Figure 11:
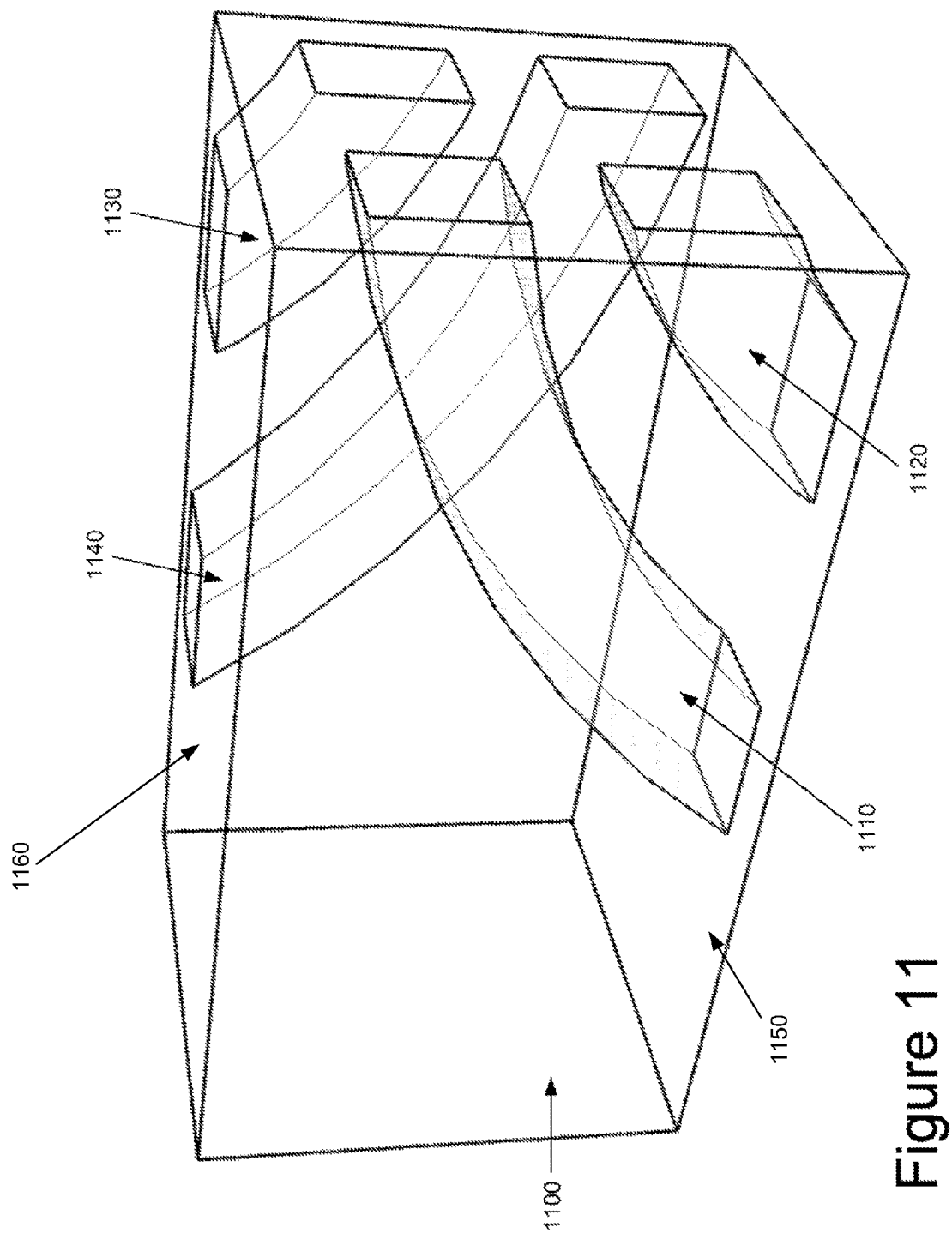
FIGS. 11 and 12 illustrate different views of an alternative fusion member embodiment whereby the tubular block channels follow semicircular arcs to reach the inferior and superior block faces.
Figure 12:
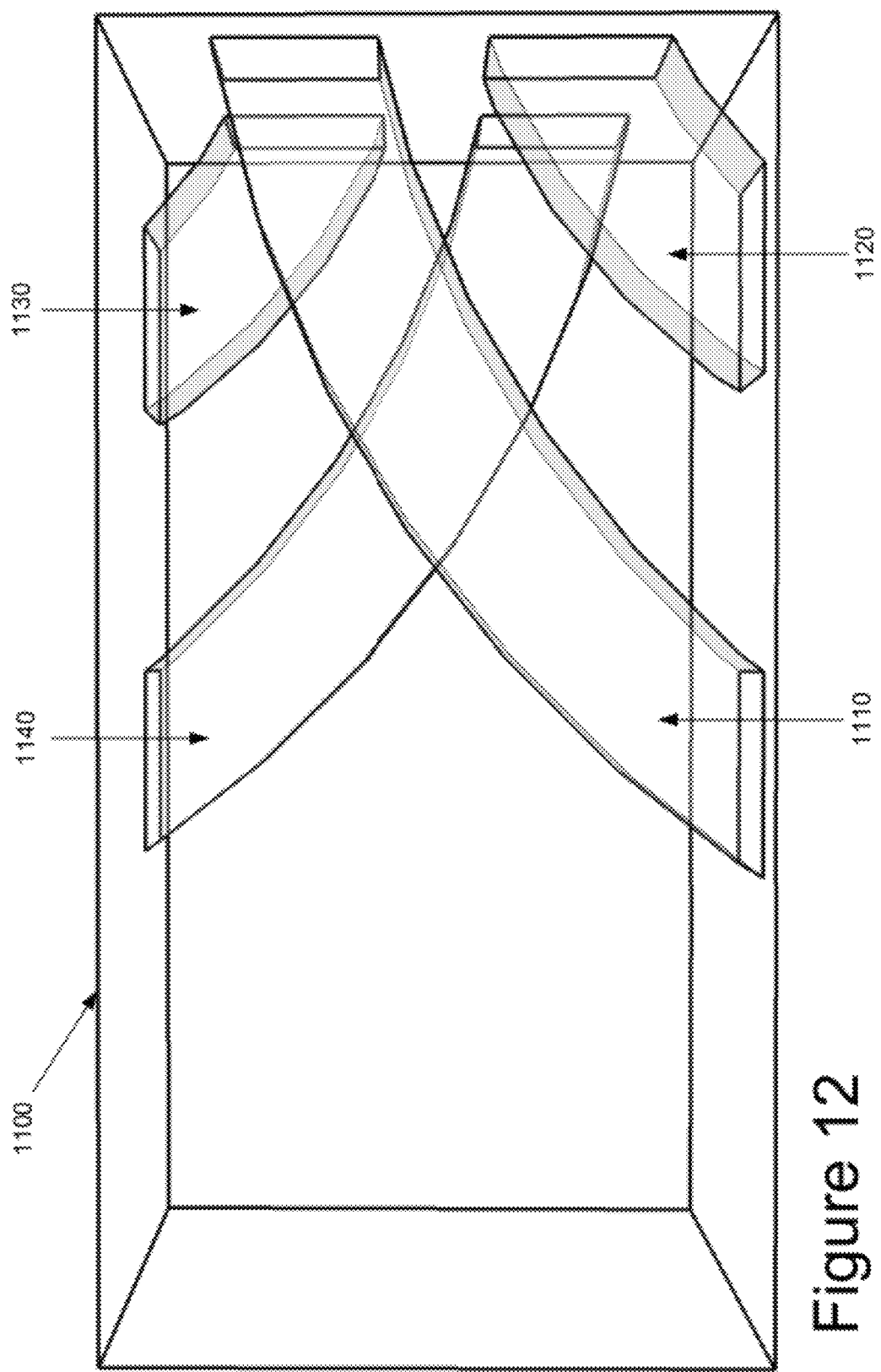
Figure 13:
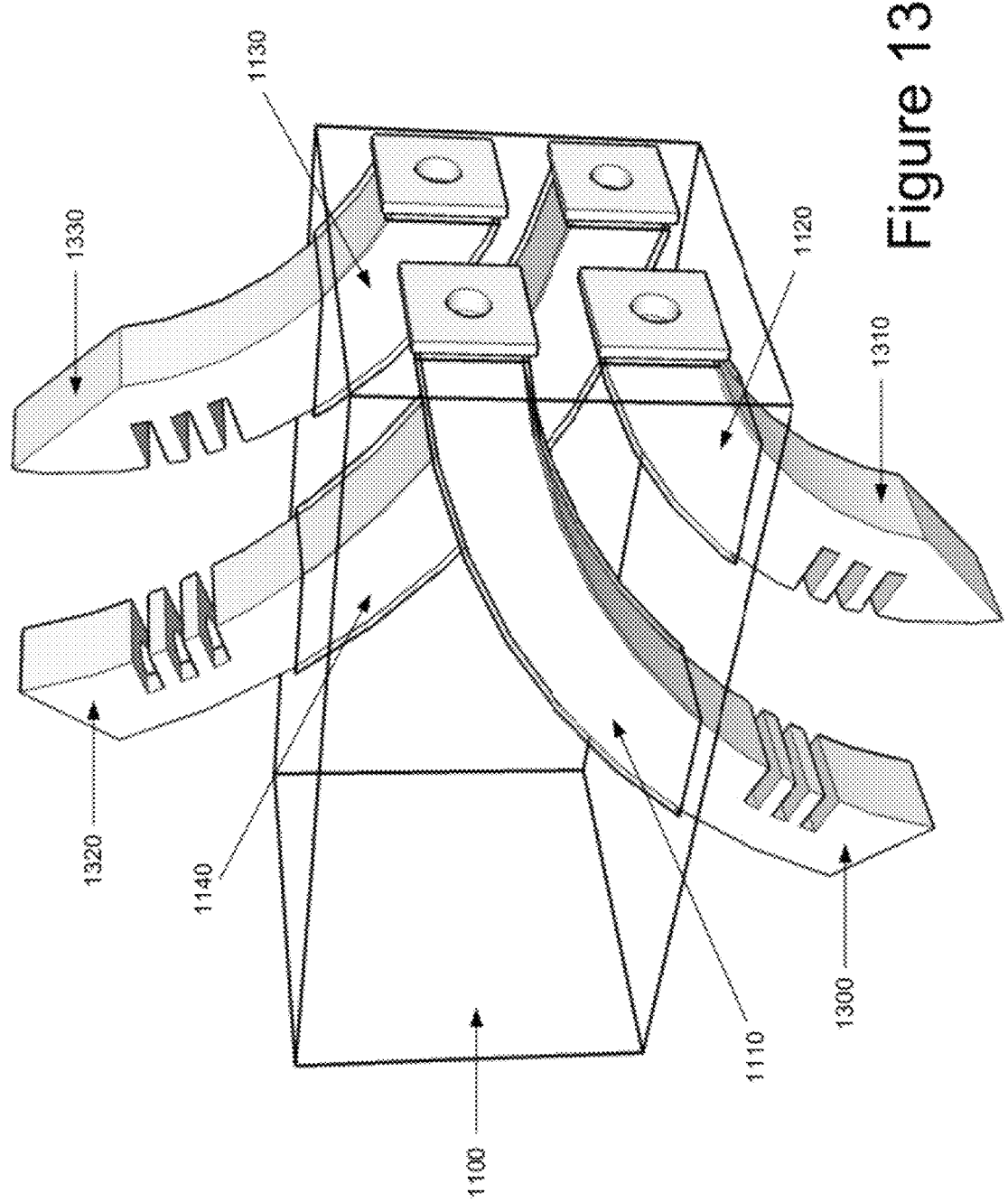
FIGS. 13 and 14 illustrate different views of needles that have been advanced through the semicircular tubular channels of the fusion member into the marrow space of the vertebral bodies.
Figure 14:
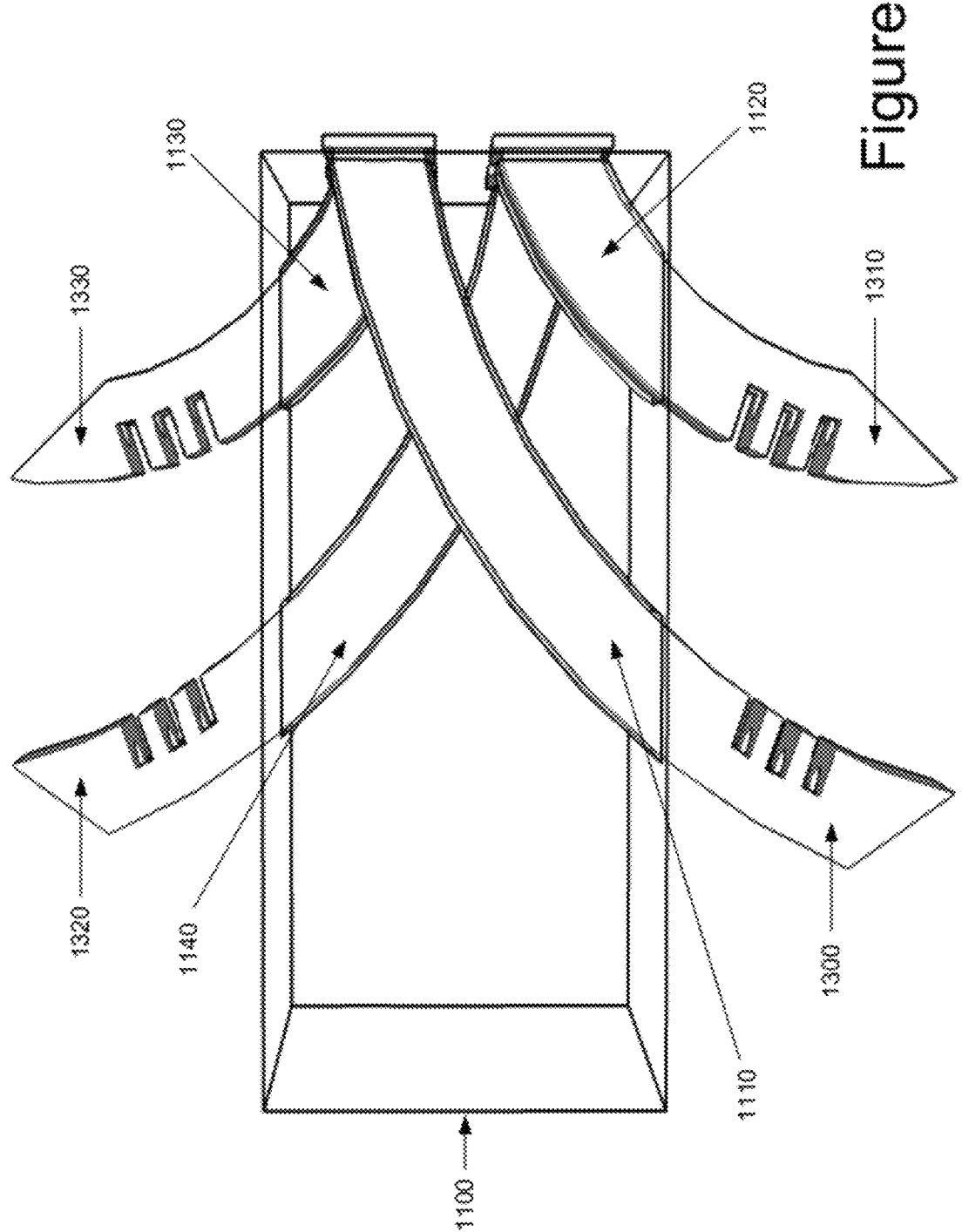

For instance, in some embodiments, the needles and the fusion-member channels are in shape of an arc. FIGS. 11-14 depict one such embodiment. In this embodiment, the tubular block channels 1110 and 1120 follow semi-circular arcs to reach the inferior block face 1150. The tubular block channels 1130 and 1140 follow semi-circular arcs to reach the superior block face 1160, as shown in FIGS. 11 and 12. These channels can be traversed by semi-circular arc shaped needles, as illustrated in FIGS. 13 and 14. Specifically, FIGS. 13 and 14 show passage of needles through these semicircular tubular channels with needles 1300 and 1310 passing into the marrow space of the vertebral body (not pictured) beneath the fusion member, and needles 1320 and 1330 passing into the vertebral body contiguous with the superior block face (not pictured). Semi-circular arc-shaped channels and needles simplify the process of inserting needles into the channels, given the small space in which the fusion member is inserted between the vertebral bodies and the difficulty in accessing the proximal openings of the fusion member within the confines of the operative field. The needles 1300 and 1310 are flexible in some embodiments, while being rigid in other embodiments. In the semi-circular arc-shaped embodiments, the needles can be more rigid as they do not need to bend to pass through the semi-circular arc-shaped channels.

Figure 15:
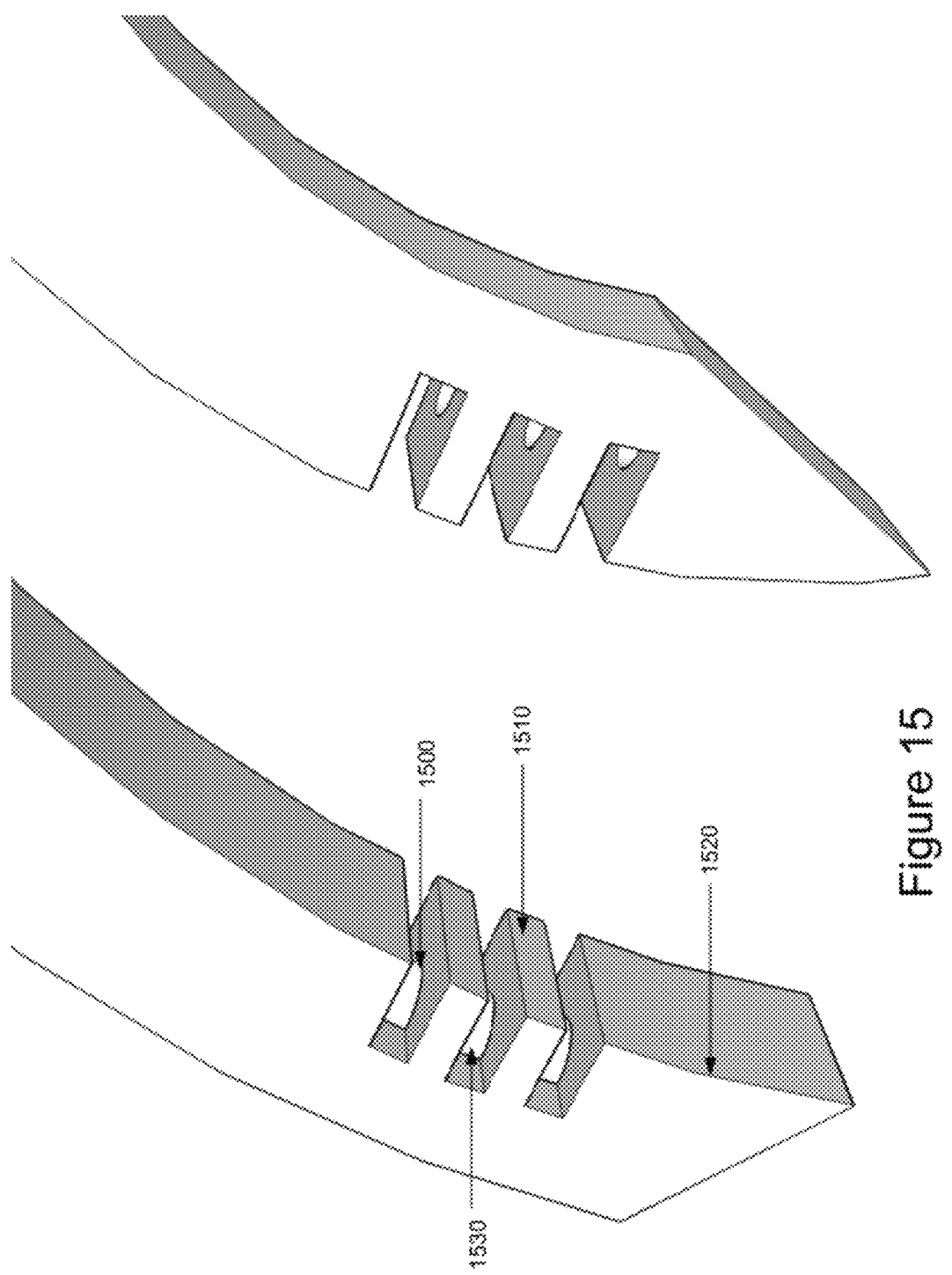
FIG. 15 illustrate a detailed view of the needle tips of one embodiment.

In some embodiments, the arcs are circular arcs as shown in FIG. 14. These circular arcs are part of two conceptual circles that are parallel to each other. FIG. 15 provides a detailed view of the needle tips of some of the arc-shaped embodiments. As shown in this figure, the central lumen 1500 of the arc-shaped needle of some embodiments is in direct communication with perforations 1530 along the needle shaft as well as the "teeth" or retention ridges. This allows the adhesive material to be delivered to the area adjacent to and between the angled teeth or retention ridges, such that these surface contours can engage the adhesive materials when it hardens, locking the needle in position within the trabecular bone, thereby locking the fusion member to the vertebral body.

Figure 16:
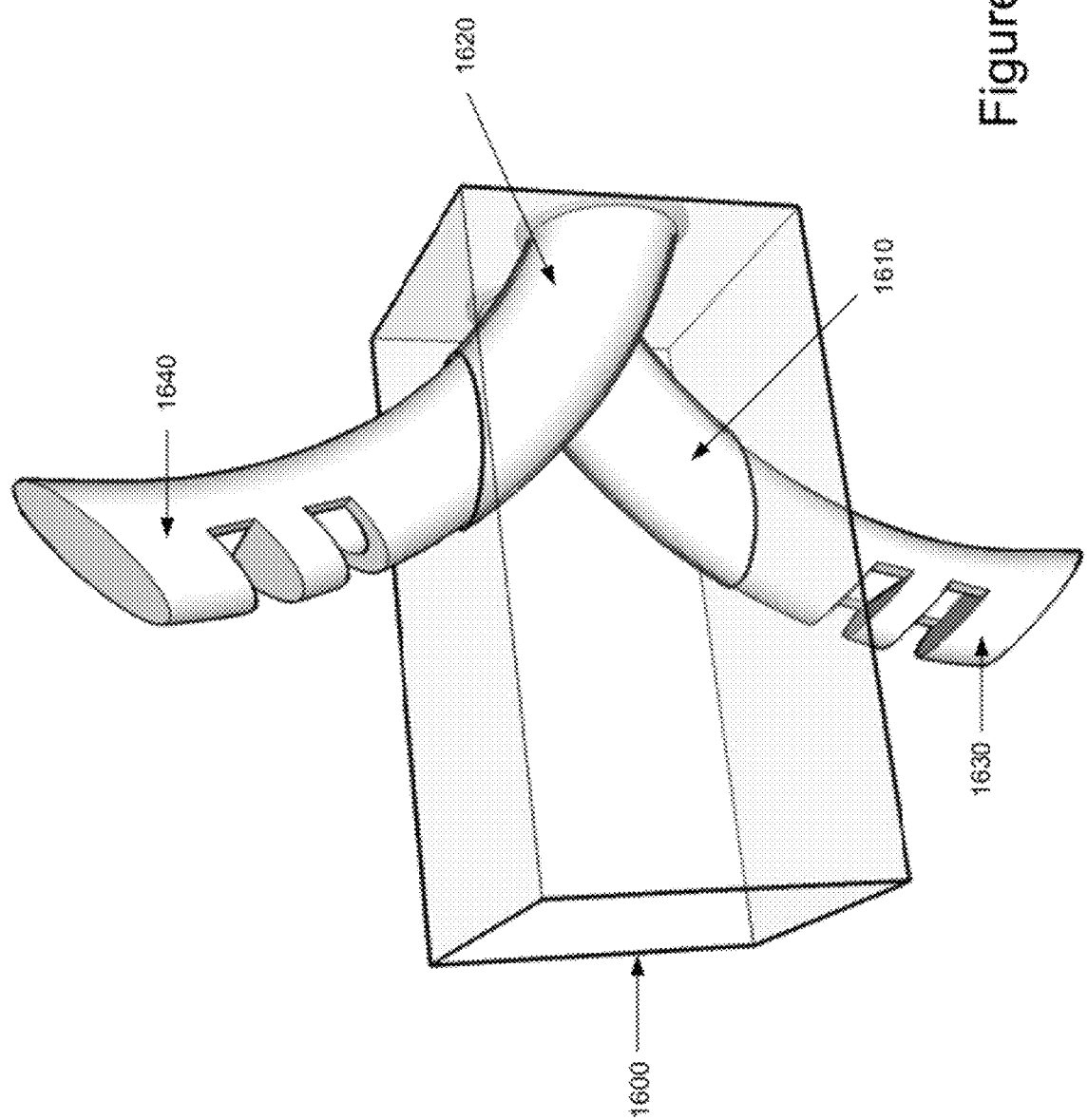
FIGS. 16-18 illustrate different views of an alternative fusion member embodiment with nonparallel angled curved channels extending to the inferior and superior block faces.
Figure 17:
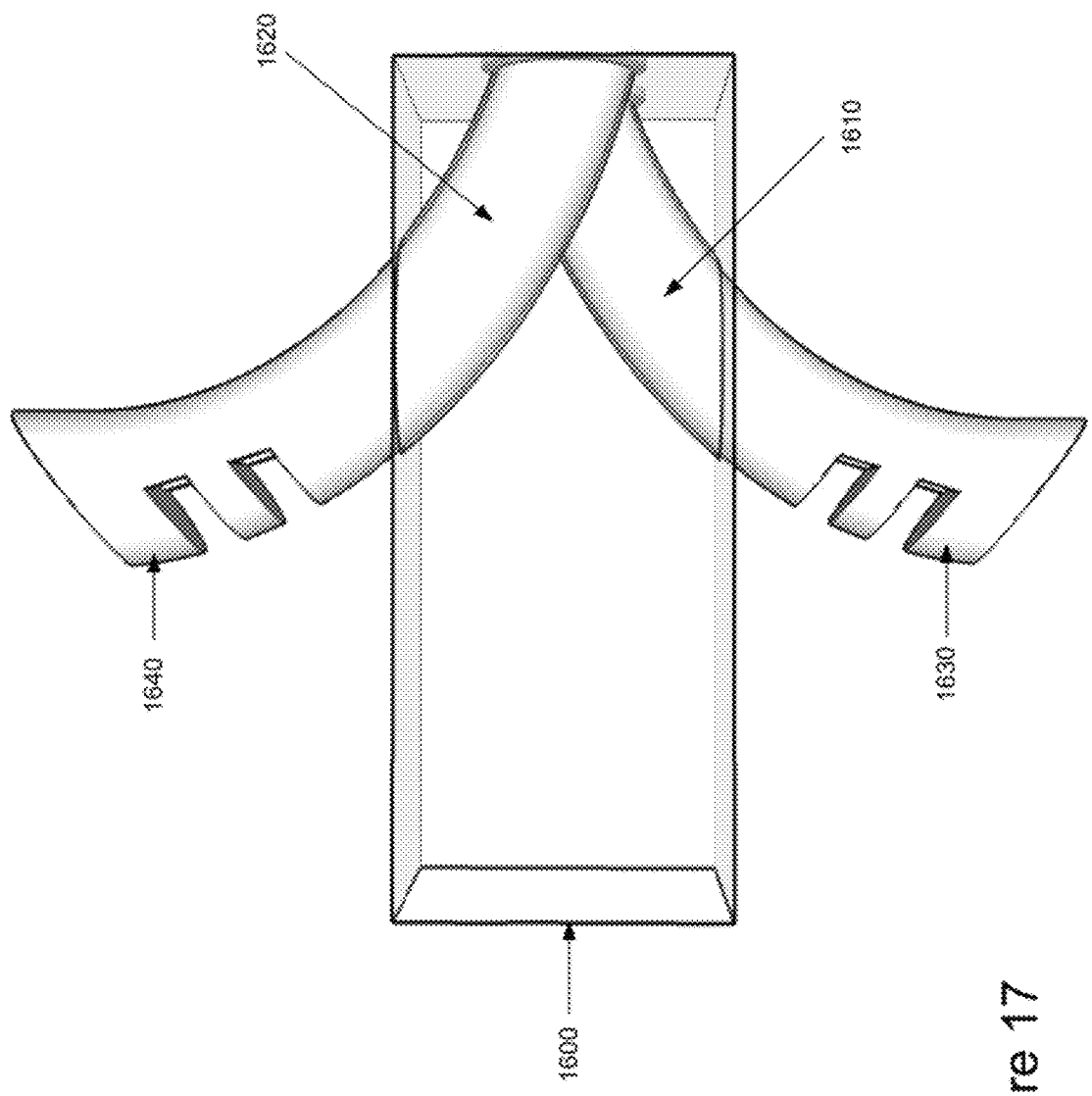
Figure 18:
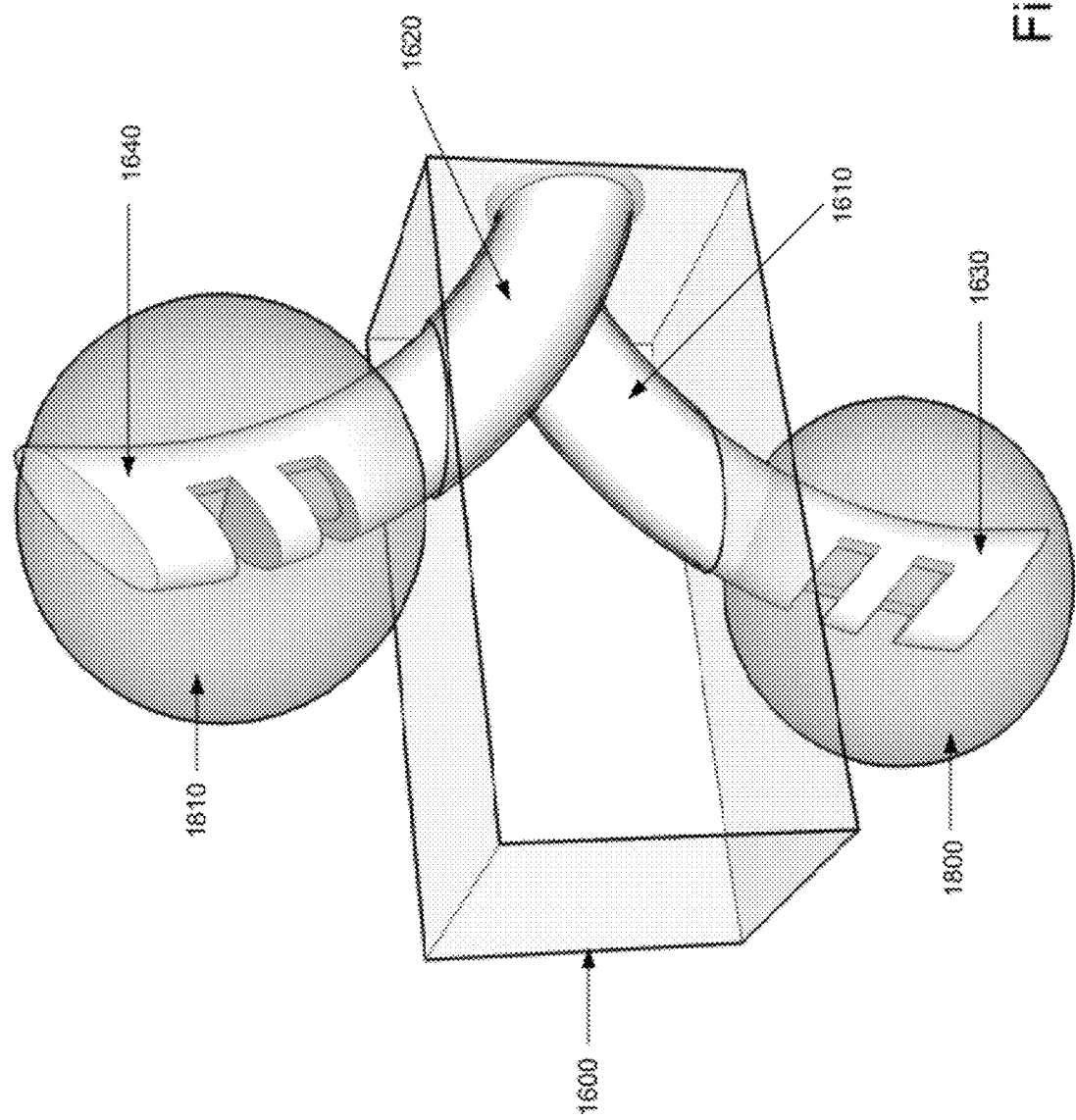

In FIGS. 16, 17, and 18, an alternate fusion member embodiment 1600 comprising two curved semicircular channels 1610 and 1620 is depicted with curved fusion needles 1630 and 1640 fully advanced through these channels into the marrow spaces of the vertebral bodies (not pictured) below and above the block. In FIG. 18, PMMA has been injected and formed collections 1800 and 1810 adjacent to the perforated, contoured tips of needles 1630 and 1640 within the marrow spaces of the adjacent vertebral bodies (not pictured).

B. Channels Traversing in all Three Dimensions

Figure 19:
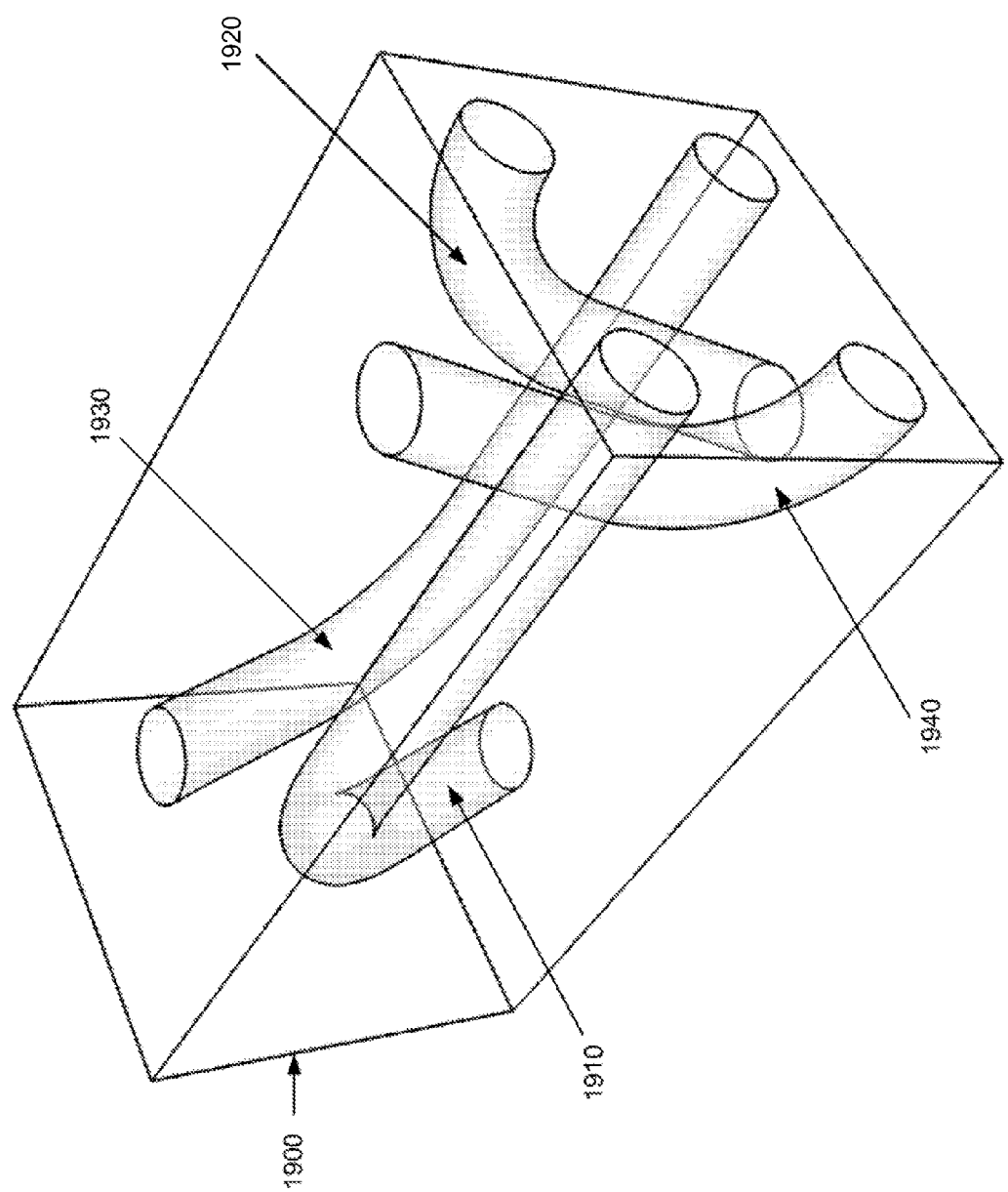
FIGS. 19-20 illustrate different views of curved needles that have been advanced through curved semicircular channels of the fusion member.
Figure 20:
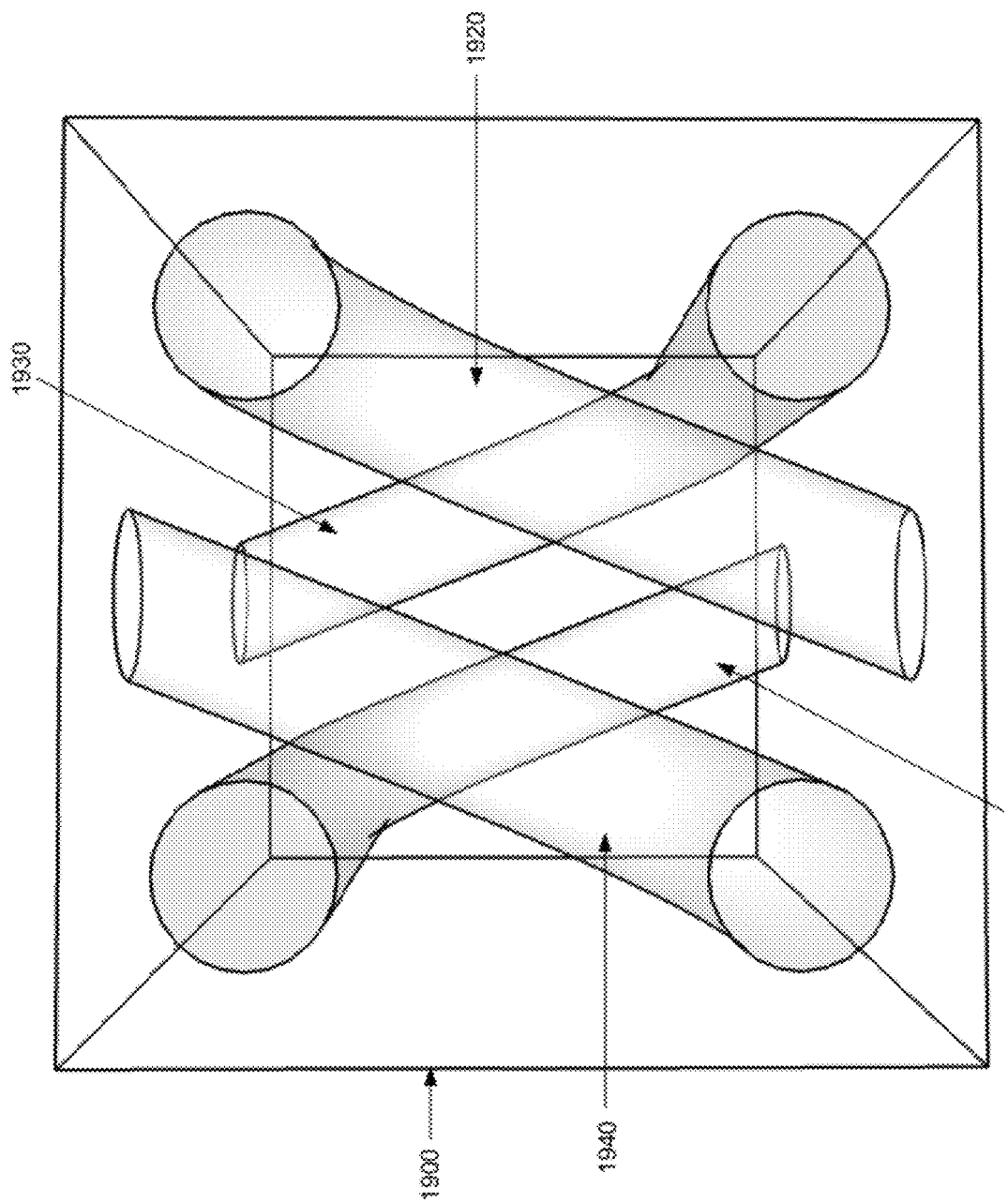
Figure 21:
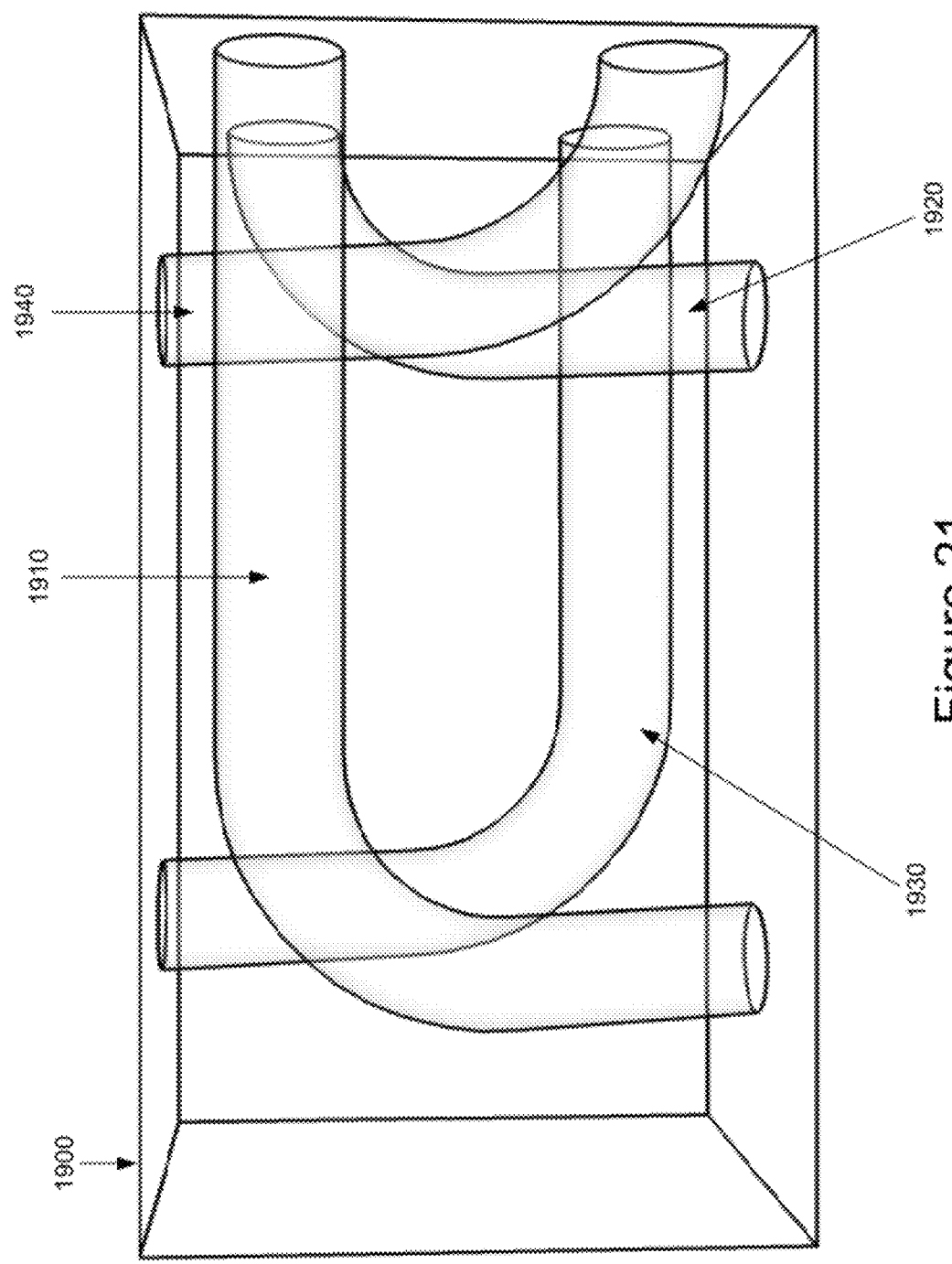
FIG. 21 illustrates the coalescence of the PMMA collections that result following injections of PMMA through the needles into the marrow space of the adjacent vertebral bodies.

Another shape that the channels can take is to have a shape that traverses in x-, y-, and z-directions. FIGS. 19, 20, and 21 depict an alternate fusion member embodiment 1900 with nonparallel angled curved channels 1910 and 1920 and nonparallel angled curved channels 1930 and 1940 extending to inferior and superior block faces, respectively.

Figure 22:
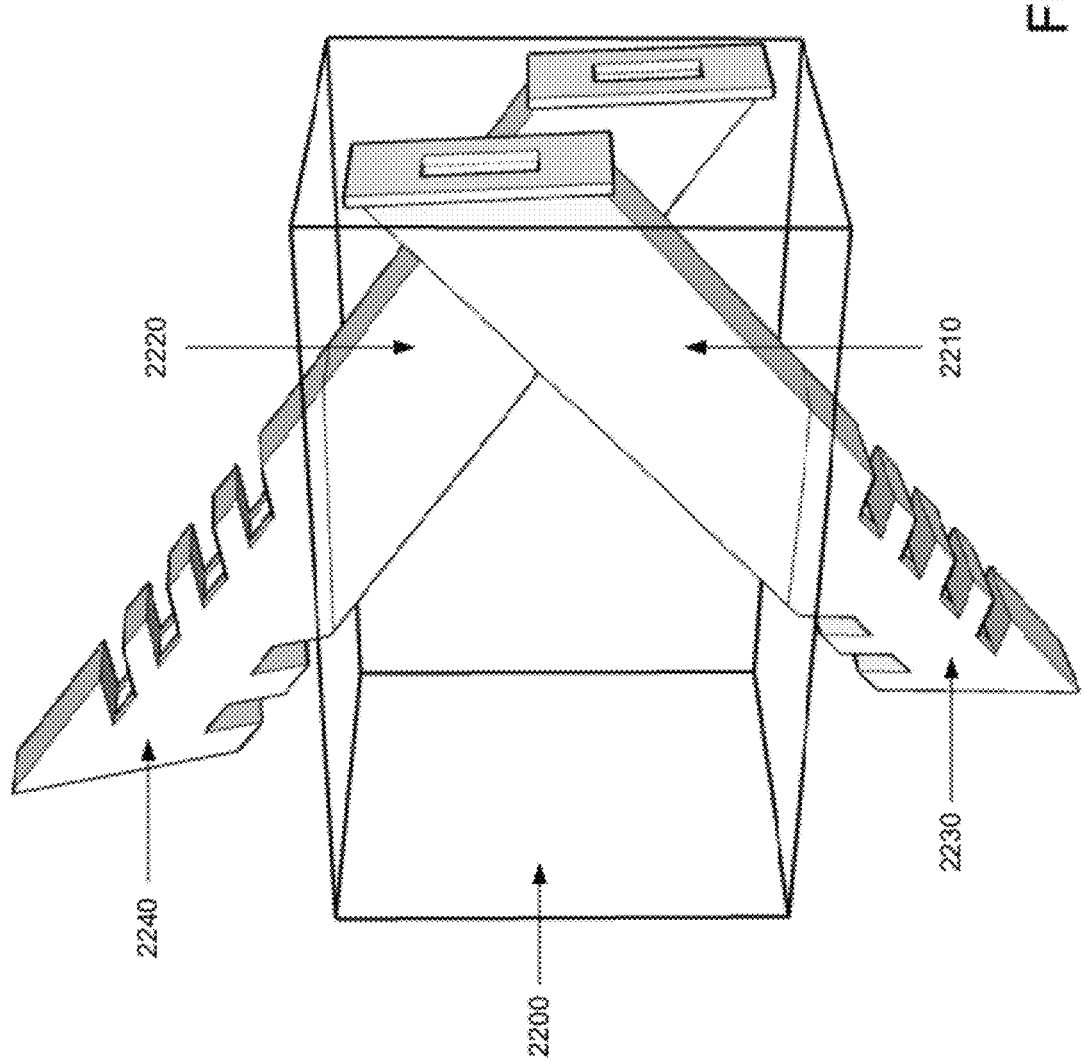
FIGS. 22 and 23 illustrate different views of an alternative fusion member embodiment comprising oblique linear channels that are traversed by straight needles which are rectangular in cross-sectional profile.
Figure 23:
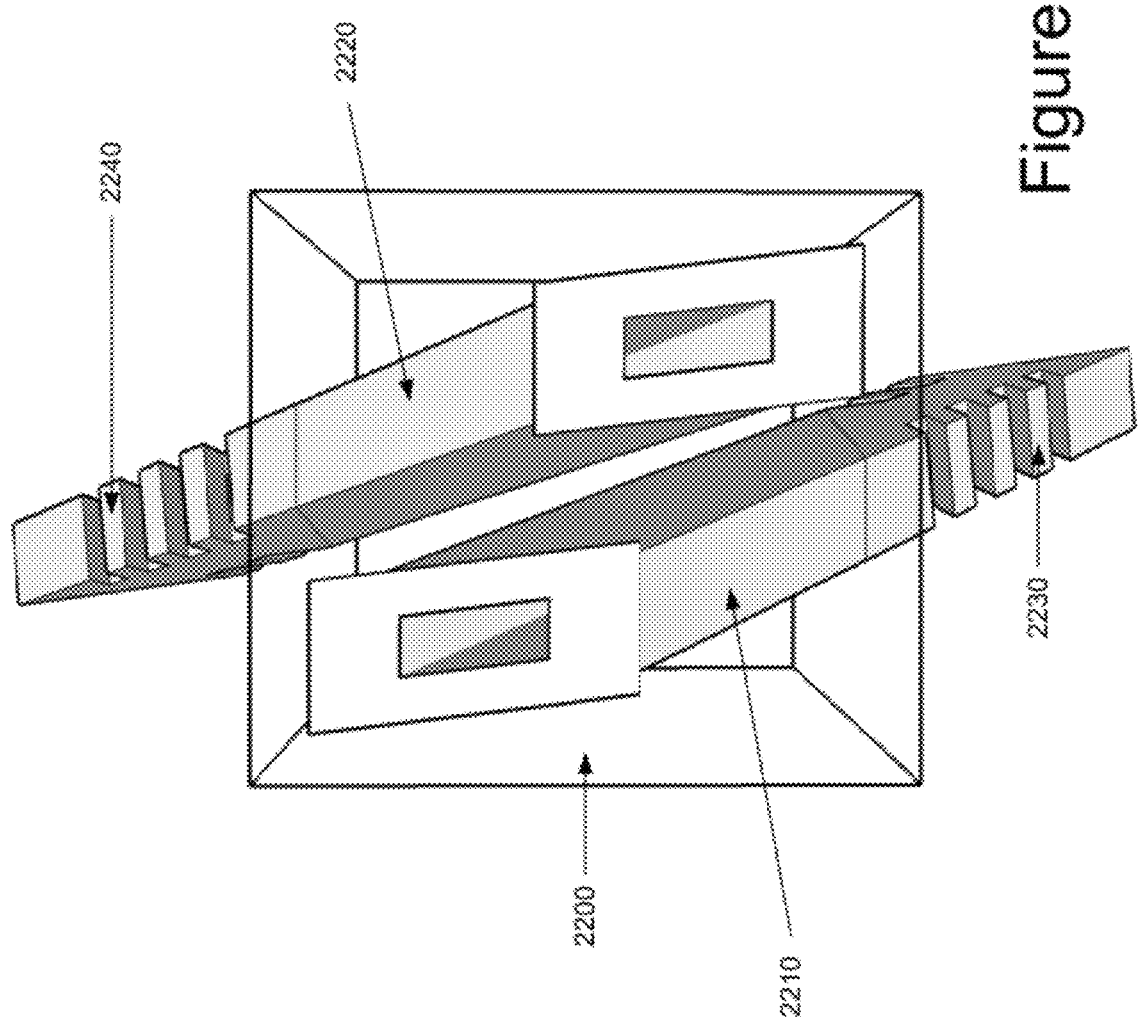
Figure 24:
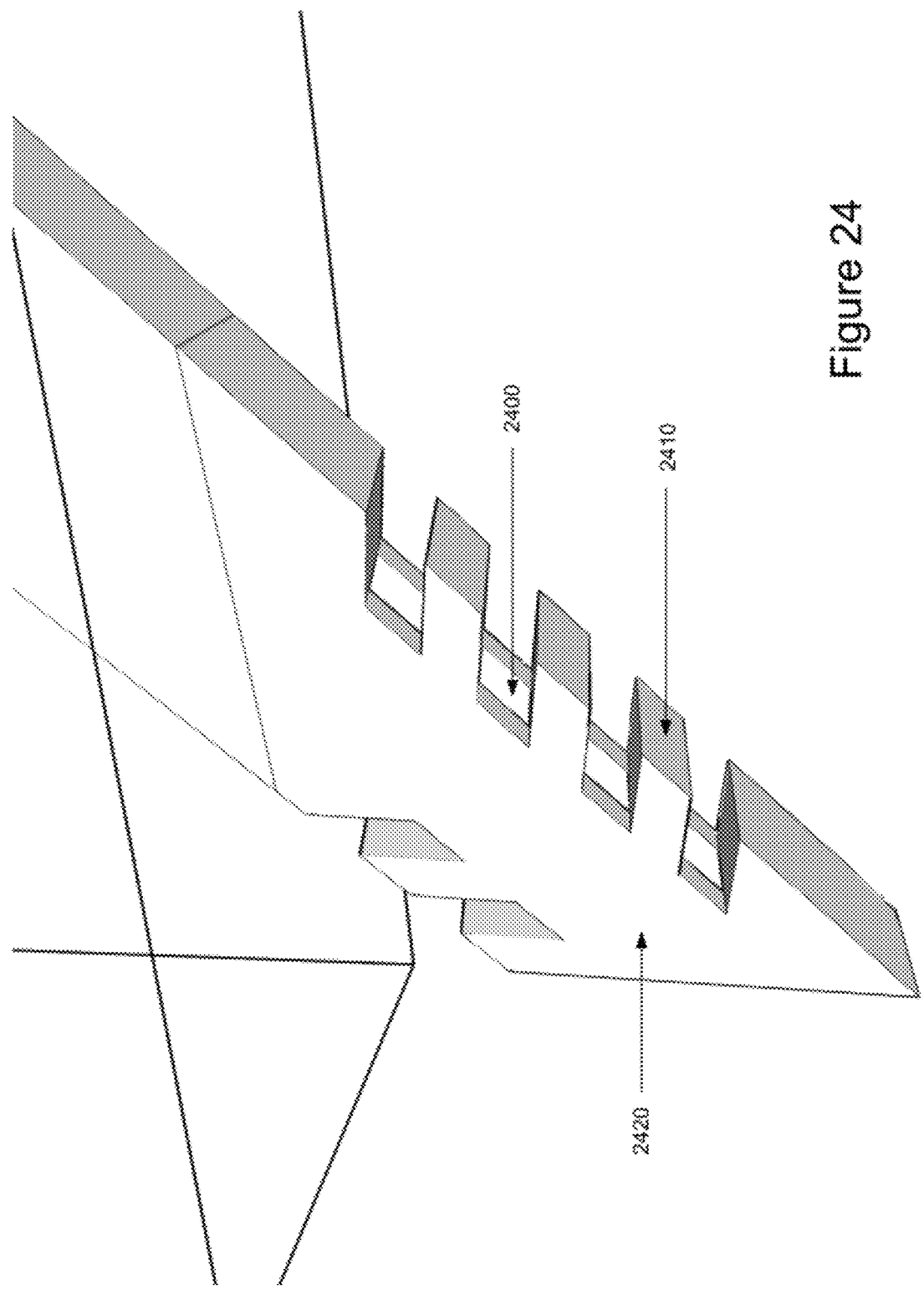
FIG. 24 illustrates a detailed view of one fusion needle embodiment.

FIGS. 22 and 23 depict an alternate embodiment of a fusion member with channels that traverse in all three directions. As shown in these figures, the block 2200 includes two oblique channels 2210 and 2220 that are traversed by needles 2230 and 2240, which are rectangular in cross-sectional profile. The distal openings of these oblique, nonparallel channels 2210 and 2220 are located at or near the geometric centers of the inferior and superior block faces. FIG. 24 provides a detailed view of one fusion needle embodiment depicting the direct communication of the central needle lumen 2400 with perforations along the needle shaft as well as the "teeth" or retention ridges 2410 and beveled tip 2420 of this embodiment. In FIGS. 25 and 26, PMMA has been injected and forms collections 2500 and 2510 contiguous with the perforated, contoured tips of needles 2230 and 2240 within the marrow spaces of adjacent vertebral bodies (not pictured).

C. Arc Shaped Channels and Needles that Traverse in all Three Dimensions

Figure 27A:
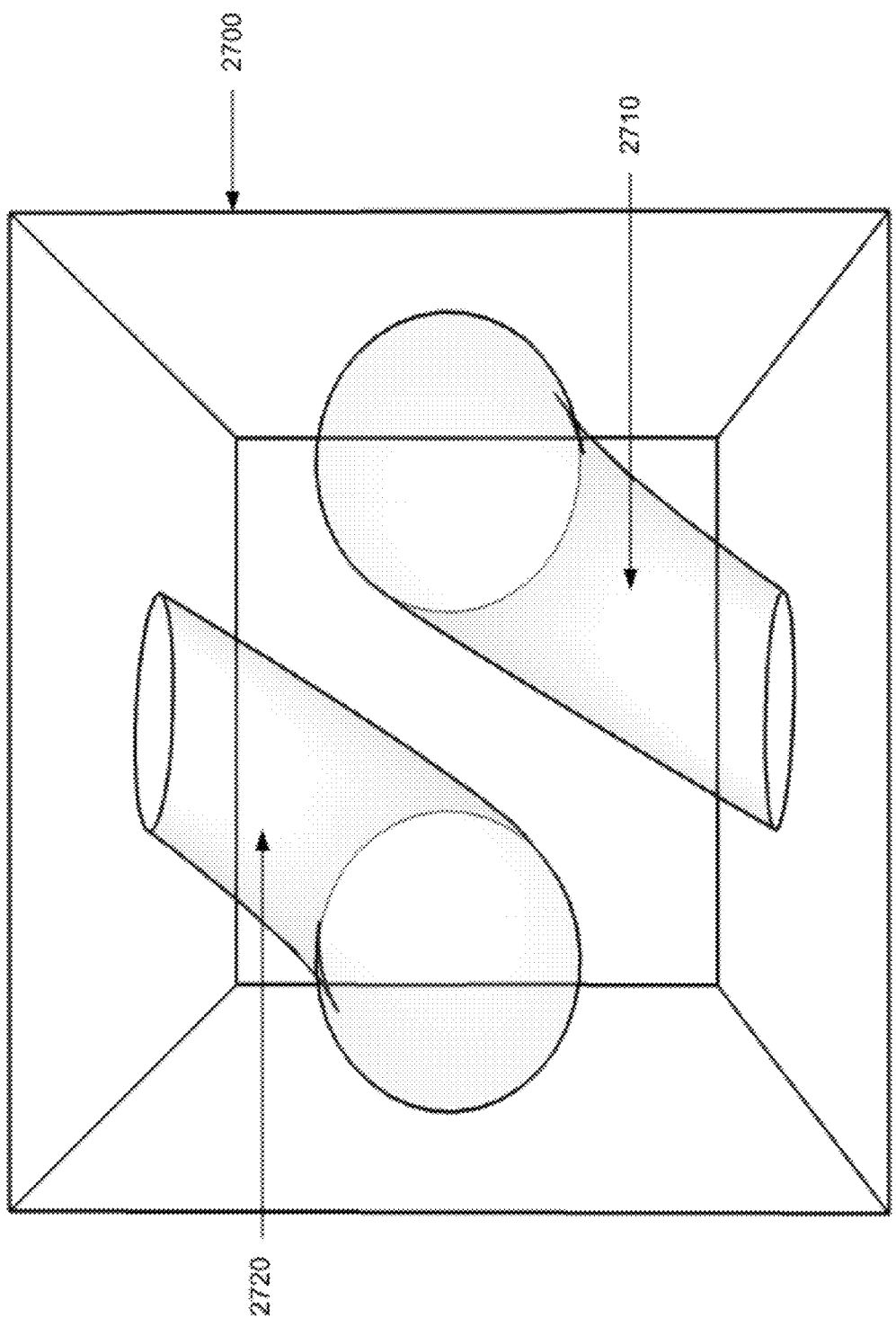
Figure 28:
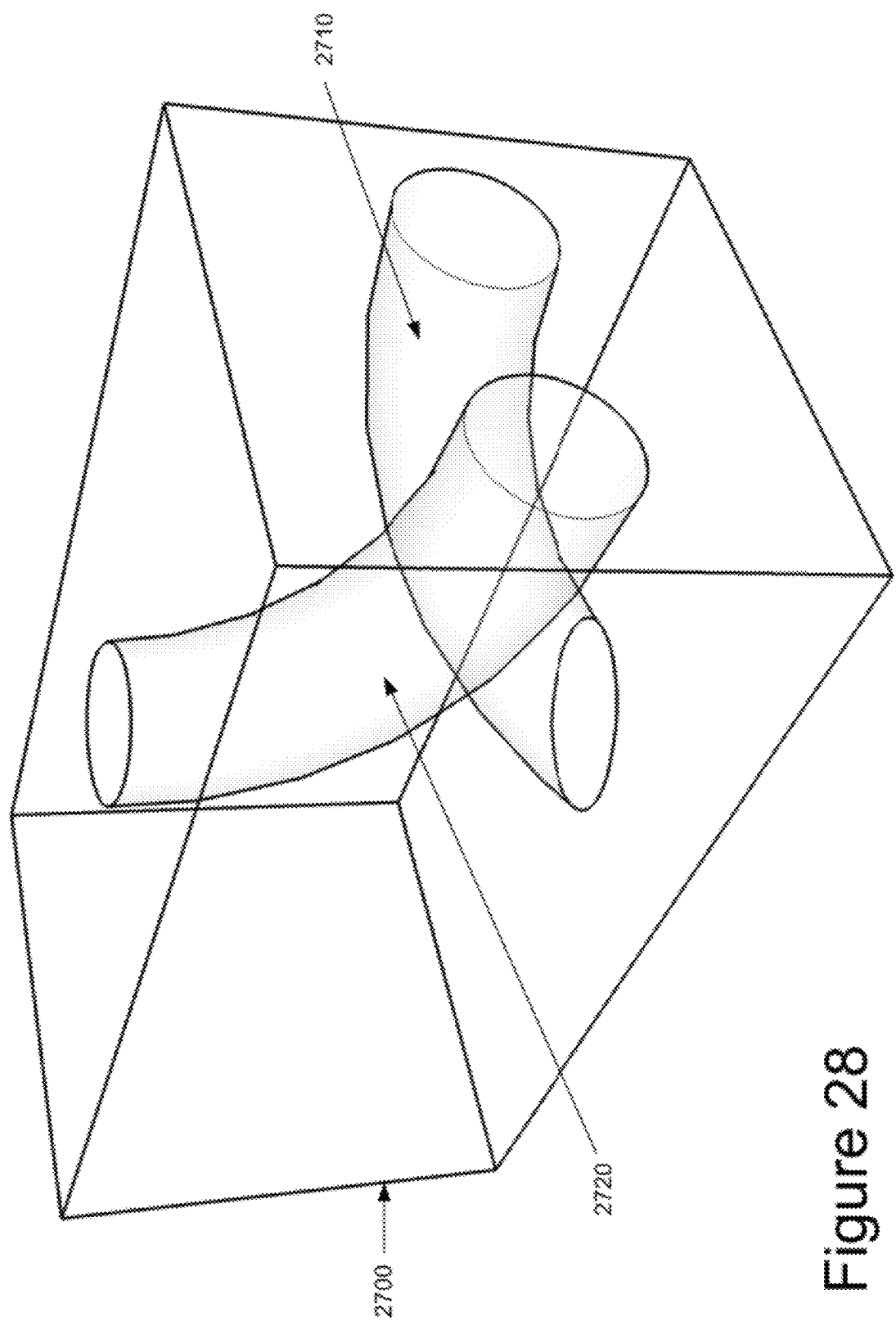

FIGS. 27a and 28 depict an alternate embodiment of a fusion member with channels that traverse in parallel planes with respect to each other but are not parallel with respect to the block faces of the fusion member. As shown in these figures, the block 2700 includes two tubular channels 2710 and 2720 that traverse in both x-, y-, and z-directions. As shown in FIG. 27b, each of the channels 2710/2720 are circular arcs that are part of two conceptual circles that are parallel to each other and oblique to all block faces. These channels are traversed by curved needles (not pictured) that also traverse in x-, y-, and z-directions. The channels and needles in this embodiment are circular arcs in their cross-sectional profiles, but they could have any other curved arc shape in other embodiments. The distal openings of these tubular, parallel channels 2710 and 2720 are located at or near the geometric centers of the inferior and superior block faces.

D. Alternative Needle Tips

Figure 29B:
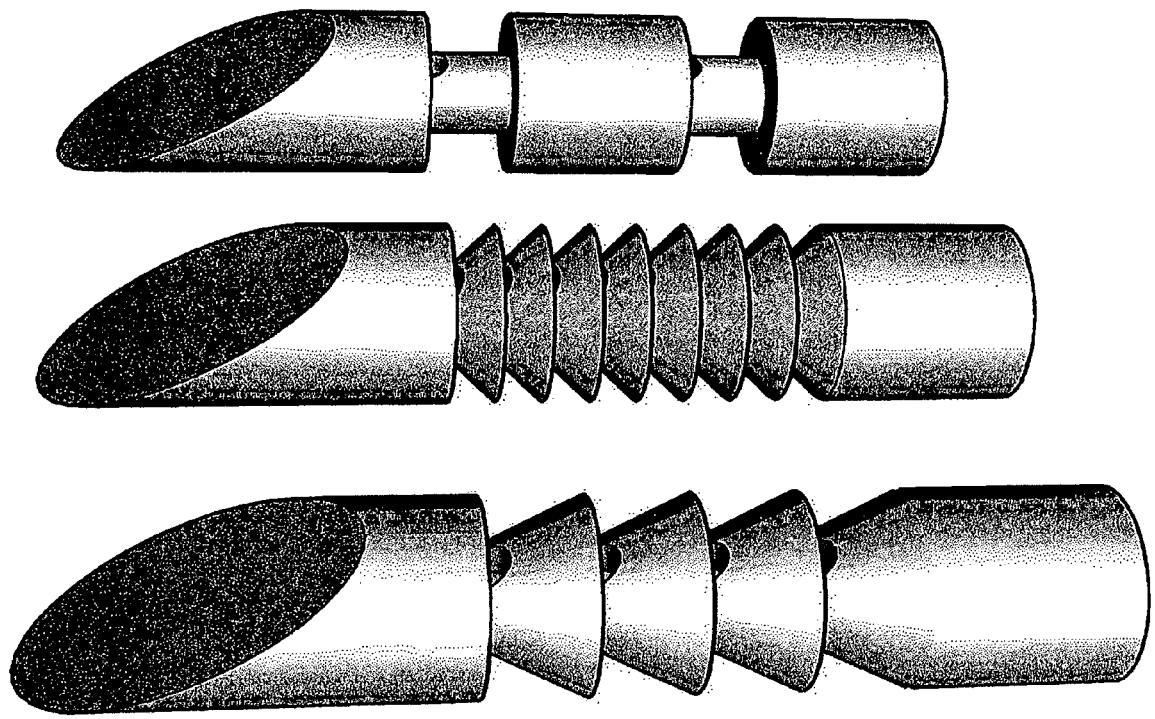

FIG. 29a provides a detailed view of alternative needle tips. In some embodiments, the needles may be arc-shaped. In other embodiments, the needles may be angled, semi-circular, arc-shaped, or straight. As shown in this figure, the central lumen 2900, 2905, and 2910 of the needle of some embodiments is in direct communication with perforations 2915, 2920, and 2925 along the needle shaft as well as the "teeth" or retention ridges 2930, 2935, and 2940. FIG. 29b illustrates that in some embodiments the needles have beveled tips.

In some embodiments, the maximum diameter or circumference of the segment of the needle that includes retention ridges or other surface features intended to engage the adhesive material (e.g., PMMA or bone cement) is less than or equal to the diameter or circumference of proximal and distal needle segments. This allows the needle to be hammered, tapped, or simply pushed into position within the marrow space of the vertebral bodies rather than being screwed into place.

E. Blocks with Ridges and Additional Bone-Grafting Channels

FIG. 30 depicts various block surface contour features including orthogonal ridges 3000, angled ridges 3010, and oblique parallel ridges 3020. Longitudinal channels 3030 and 3040 and transverse channels 3050 and 3060 for positioning and retention of bone graft material are also illustrated. These surface contours and retention channels may be combined with any of the fusion needle channel configurations previously described. Bone grafting channels allow for the positioning of bone grafting material between and in contact with the opposed endplates of the adjacent vertebral bodies. Placement of the bone graft material in the disc space surrounding the fusion member permits the progressive solid bony fusion between the fusion member and the adjacent vertebral bodies.

V. FUSION PROCEDURE

Figure 31:
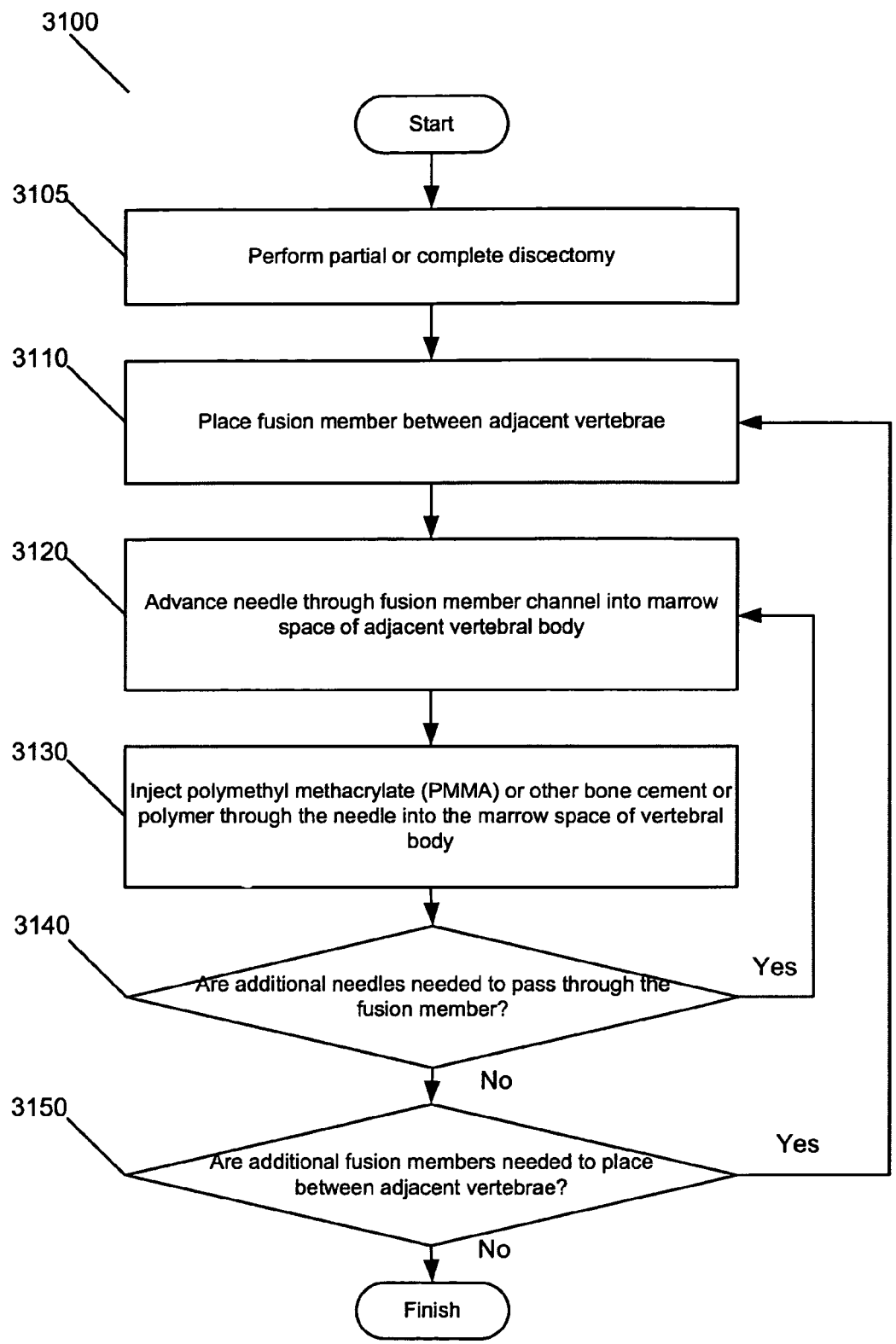
FIG. 31 illustrates an exemplary fusion procedure.

FIG. 31 depicts a medical procedure 3100 that involves the insertion of the fusion device of some embodiments of the invention. In this procedure, a caregiver (e.g., a physician) initially performs (at 3105) a partial or complete discectomy, which typically involves making an incision in the patient and removing the disc between two vertebral bodies. Any number of known techniques/procedures can be used to remove the disc at 3105.

Next, the caregiver positions (at 3110) an interbody fusion member (e.g., one of the blocks described above) with one or more tubular channels between the endplates of adjacent vertebrae. Any number of known technique/procedures for inserting a block between two adjacent vertebrae can be used (at 3110) to insert the interbody fusion member between adjacent vertebrae.

The block faces are in contact with the opposed endplates. These faces may be parallel to each other, or nonparallel such that the fusion member presents a tapered profile when viewed laterally so as to restore both disc height and physiologic lordosis.

Once properly positioned, a large gauge needle (at 3120) is (1) passed through a channel of the fusion member inserted at 3110 and (2) advanced into the marrow space of the adjacent vertebral body. In some embodiments, a flange at the base of each needle fits into a recess of increased diameter where the tubular channel meets the exposed block surface locking the needle's position and anchoring it to the block. These needles may be open or closed at their tips and perforations of various spacing and configuration along the needle shafts communicate directly with a central lumen, which extends to the needle base. In some embodiments, various surface contours along the needle shaft, including angled teeth and backfacing ridges, allow the needle to be passed through the block's channel and into the bone but prevent it from being easily withdrawn from the bone, enhancing structural integrity.

In some embodiments, the inserted needle is tapped at its proximal end in order to cause its distal end to penetrate the vertebral body, which the needle encounters as it exits the fusion-member channel in which it is inserted. To facilitate this penetration, some embodiments insert a smaller gauge needle into this channel and into the marrow space of the adjacent vertebral body before inserting the large-gauge needle at 3120. This creates a guide to help ensure the large gauge needle will be advanced into the proper position within the trabecular bone of the vertebral body.

Once a needle is in position, polymethyl methacrylate (PMMA), other bone cement or polymer, or other adhesive may be injected (at 3130) through the needle and pass through its openings/perforations into the marrow space of the vertebral body, ideally forming a spherical or ellipsoidal "cloud" of adhesive material (e.g., PMMA) contiguous with the needle tip.

In some embodiments, one or more needle(s) are advanced through multiple channels of a fusion member into the same vertebral body and PMMA or other bone cement or polymer injected through these needles. Accordingly, after 3130, a determination is made (at 3140) whether additional needles need to be inserted into the fusion member inserted at 3110. If so, another needle is pushed (at 3120) through another channel of the fusion member, and adhesive material is injected (at 3130) into this other needle and through its openings/perforations into the marrow space of vertebral body. The resultant adhesive (PMMA) clouds from adjacent needle tips may unite to form a single larger cloud upon polymerization, with multiple contoured and perforated needles locked to the fusion member and anchored to the solid PMMA and trabecular bone of the vertebral body. One or more additional needles may be passed (at 3120) through additional channels and into the marrow space of the vertebral body contiguous with the opposite face of the fusion member and the injection process repeated. The final result is an intervertebral fusion member anchored via multiple contoured, perforated needles to collections of PMMA and to the trabecular bone of adjacent vertebral bodies yielding solid mechanical fusion.

In some embodiments, more than one fusion member is inserted between two adjacent vertebral bodies. Accordingly, a determination is made (at 3150) whether another fusion member needs to be inserted between the vertebral bodies between which the last fusion member was inserted at 3110. If so, the medical procedure is repeated from 3110 to 3150. Also, in some embodiments, the medical procedure 3100 is performed multiple times to replace multiple discs between multiple pairs of vertebral bodies.

VI. EMBODIMENTS THAT DO NOT USE ADHESIVE MATERIALS

In some embodiments, the needles may be without a central lumen or perforations along their shaft. In some embodiments, angled teeth, backfacing ridges, and other surface retention ridges may be greater in circumference or diameter than the more proximal or distal needle segments. In these instances, after the needles are advanced into the marrow space of the vertebral bodies, injection of adhesive materials may not be needed to anchor the vertebral bodies to the fusion member. The surface contours of the needles will anchor the vertebral bodies to the fusion member.

While the invention has been described with reference to numerous specific details, one of ordinary skill in the art will recognize that the invention can be embodied in other specific forms without departing from the spirit of the invention. For example, prior to advancing a large gauge needle through the fusion member channel into the marrow space of the vertebral body, some embodiments of this invention may insert a smaller gauge needle through the fusion member channel into the marrow space of the vertebral body and then remove the smaller gauge needle to create a guiding channel for placement of the large gauge needle into the proper position within the trabecular bone or the marrow space of the vertebral body.

Also, in several of the above-described embodiments, the channels and needles have circular-arc cross-sectional profiles. However, in other embodiments, the channels and needles have alternative curved arc shapes.

The invention claimed is:

1. A method of positioning a fusion member with at least one curved channel between two vertebral bodies, the method comprising:

inserting at least one needle into a vertebral body by advancing the needle through the curved channel, wherein the needle has a first end and a second end, wherein the needle is made at least partially of flexible material, wherein the needle has a lumen for receiving hardening material;

tapping at the first end of the needle so that the second end of the needle enters the vertebral body; and supplying hardening material through the lumen to a location where the needle is inserted into the vertebral body, said hardening material for bonding the needle to the vertebral body.

2. The method of claim 1, wherein the needle comprises at least one perforation for supplying the hardening material through to the location where the needle is inserted into the vertebral body.

3. The method of claim 1, wherein the hardening material comprises at least one of polymethyl methacrylate (PMMA), bone cement, and bone polymer.

4. The method of claim 2, wherein the perforation communicates directly with the lumen.

5. The method of claim 1, wherein the needle comprises surface contours, said surface contours for preventing a withdrawal of the needle from the vertebral body when engaged with the hardening material.

6. The method of claim 5, wherein a part of the needle comprising the surface contours has a circumference that is less than the circumference of another part of the needle adjacent to the surface contours.

* * * * *